United States Patent
Barbé et al.

(10) Patent No.: US 7,354,602 B2
(45) Date of Patent: *Apr. 8, 2008

(54) CONTROLLED RELEASE CERAMIC PARTICLES, COMPOSITIONS THEREOF, PROCESSES OF PREPARATION AND METHODS OF USE

(75) Inventors: Christophe Jean Alexandre Barbé, Abbotsford (AU); John Bartlett, Towradgi (AU)

(73) Assignee: Australian Nuclear Science & Technology Organisation, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/841,669

(22) Filed: Aug. 20, 2007

(65) Prior Publication Data

US 2007/0292526 A1    Dec. 20, 2007

Related U.S. Application Data

(63) Continuation of application No. 10/204,462, filed as application No. PCT/AU01/00173 on Feb. 21, 2001, now Pat. No. 7,258,874.

(30) Foreign Application Priority Data

Feb. 21, 2000    (AU) .................................... PQ 5733

(51) Int. Cl.
    *A61K 9/50*    (2006.01)
(52) U.S. Cl. ................... 424/501; 424/400; 424/489
(58) Field of Classification Search ..................... None
    See application file for complete search history.

(56) References Cited

U.S. PATENT DOCUMENTS

| | | | |
|---|---|---|---|
| 3,923,969 A | 12/1975 | Baukal et al. | |
| 4,293,540 A | 10/1981 | Shikita et al. | |
| 4,489,055 A | 12/1984 | Couvreur et al. | |
| 5,085,861 A | 2/1992 | Gerhart et al. | |
| 5,112,676 A | 5/1992 | Cot et al. | |
| 5,451,581 A | 9/1995 | Lee et al. | |
| 5,591,463 A | 1/1997 | Ducheyne et al. | |

(Continued)

FOREIGN PATENT DOCUMENTS

CA        2438438        2/2005

(Continued)

OTHER PUBLICATIONS

Asefa, et al., "Periodic Mesoporous Organosilicas with Organic Groups inside the Channel Walls", *Nature*, Dec. 1999, vol. 402, Nos. 23/30, p. 867-871.

(Continued)

*Primary Examiner*—Michael P. Woodward
*Assistant Examiner*—Eric E. Silverman
(74) *Attorney, Agent, or Firm*—Foley & Lardner LLP

(57) ABSTRACT

Controlled release ceramic particles, processes for their preparation, controlled release ceramic particles prepared by such processes, compositions comprising such controlled release ceramic particles and methods of using controlled release ceramic particles are described. In one form each of the controlled release ceramic particles has an active material(s) substantially homogeneously dispersed throughout the particles, wherein the active material(s) is capable of being released from said particles, and the active material(s) in said particles is substantially protected from degradation until release of the active material(s) from the particles.

20 Claims, 25 Drawing Sheets

U.S. PATENT DOCUMENTS

| | | | |
|---|---|---|---|
| 5,731,261 | A | 3/1998 | Balducci et al. |
| 5,770,172 | A | 6/1998 | Linehan et al. |
| 5,830,480 | A | 11/1998 | Ducheyne et al. |
| 6,280,770 | B1 | 8/2001 | Pather et al. |
| 6,303,290 | B1 | 10/2001 | Liu et al. |
| 6,350,462 | B1 | 2/2002 | Hakamatsuka et al. |
| 6,413,489 | B1 | 7/2002 | Ying et al. |
| 6,559,070 | B1 | 5/2003 | Mandal |
| 6,696,258 | B1 | 2/2004 | Wei et al. |
| 6,719,989 | B1 | 4/2004 | Matsushima et al. |
| 6,869,584 | B2 | 3/2005 | Ying et al. |
| 7,037,517 | B2 | 5/2006 | Kataoka et al. |
| 7,166,570 | B2 | 1/2007 | Hunter et al. |
| 7,241,736 | B2 | 7/2007 | Hunter et al. |
| 2002/0122828 | A1 | 9/2002 | Liu |
| 2004/0180096 | A1 | 9/2004 | Prasad et al. |
| 2005/0048127 | A1 | 3/2005 | Brown et al. |
| 2005/0152832 | A1 | 7/2005 | Ying et al. |
| 2005/0281884 | A1 | 12/2005 | Adair et al. |
| 2006/0073205 | A1 | 4/2006 | Ohta et al. |
| 2006/0165787 | A1 | 7/2006 | Moerck et al. |
| 2006/0210634 | A1 | 9/2006 | Moerck et al. |

FOREIGN PATENT DOCUMENTS

| | | |
|---|---|---|
| DE | 10207504 | 2/2002 |
| DE | 10211600 | 3/2002 |
| EP | 1257259 | 8/2001 |
| GB | 1376277 | 4/1975 |
| GB | 1590574 | 6/1981 |
| GB | 2257438 | 1/1993 |
| JP | 3161429 | 7/1991 |
| KR | 20020073849 | 9/2002 |
| KR | 20040029871 | 4/2004 |
| WO | WO 97/45367 | 12/1997 |
| WO | WO 0050349 | 8/2000 |
| WO | WO 2004067508 | 8/2004 |
| WO | WO 2005117844 | 12/2005 |
| WO | WO 2006017336 | 2/2006 |
| WO | WO 2006017337 | 2/2006 |

OTHER PUBLICATIONS

Brannon-Peppas, et al., "Polymers In Controlled Release", *Polymer News*, 1997, vol. 22, No. 9, pp. 316-318.

Carli, "Microspheres and Nanoparticles for Drug Delivery Systems," *La Chimica & L'Industria*, 1993, vol. 79, No. 6, pp. 494-499.

Falaize, et al., "In Vitro Behavior of Silica-Based Xerogels Intended as Controlled Release Carriers", *J. Am. Ceram. Soc.*, 1999, vol. 82, No. 4, pp. 969-976.

Hench, "Sol-gel Materials for Bioceramic Applications", *Current Opinion in Solid State and Materials Science*, 1997, vol. 2, pp. 604-610.

Jacobs, et al., "Polymer Delivery Systems Properties and Applications", Eds. M.A. Nokely, D.M. Piatt and B.A. Charpentier, ACS Symposium Series No. 520, 1993, Ch. 1.

Kortesuo, et al., "Sol-gel-processed Sintered Silica Xerogel as a Carrier in Controlled Drug Delivery", *J. Biomed Mater. Res.*, 1999, vol. 44, pp. 162-167.

Price, "Polymers for Controlled Drug Delivery", Ed. P.J. Tarcha, CRC Press 1991, Ch. 1, pp. 1-14.

Santos, et al., "Sol-gel Derived Carrier for the Controlled Release of Proteins", *Biomaterials*, 1999, vol. 20, pp. 1695-1700.

Schmidt, Multifunctional Inorganic-Organic Composite sol-gel Coatings for Glass Surfaces, *Journal of Non-Crystalline Solids*, 1994, vol. 178, pp. 302-312.

Patent Abstracts of Japan, JP 3294221 (NGK Spark Plug Co. Ltd.), Dec. 25, 1991.

Patent Abstracts of Japan, JP 6298639 (Olympus Optical Co. Ltd.), Oct. 25, 1994.

Patent Abstracts of Japan, JP 63159313 (Olympus Optical Co. Ltd.), Jul. 2, 1988.

Patent Abstracts of Japan, JP 63159314 (Olympus Optical Co. Ltd.), Jul. 2, 1988.

Praxair Material Safety Data Sheet for Tetraethoxysilate, Jun. 2000.

Thoma, et al., "Biodegradierbare gentamin-Depotimplantate aus Beta-Tricalciumphosphatkeramik," *Pharmazie*, 1991, vol. 46, No. 3, pp. 198-202.

Moriya, et al., "Preparation of $SiO_2$—$TiO_2$ Spherical Particles by W/O—Type Emulsion Technique", *Journal of the Ceramic Society of Japan*, Int. Edition, 1995, vol. 103, pp. 570-575.

FIG. 1-1: Influence of D on the release from gels synthesised with W=8
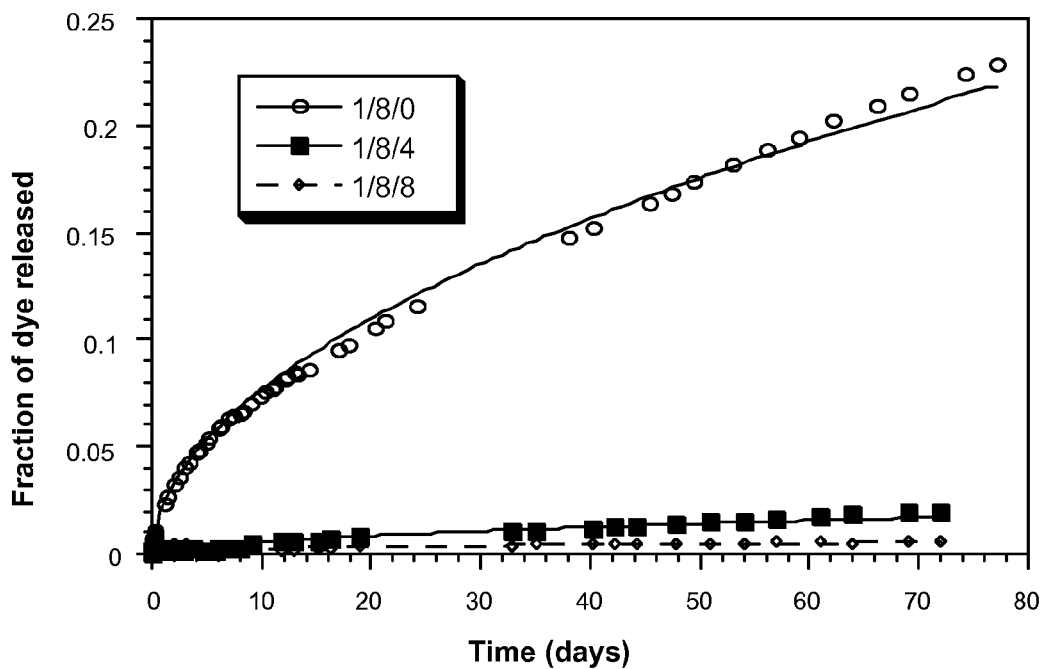
FIG. 1-2: Influence of W on the release from gels synthesised without methanol (D=0)
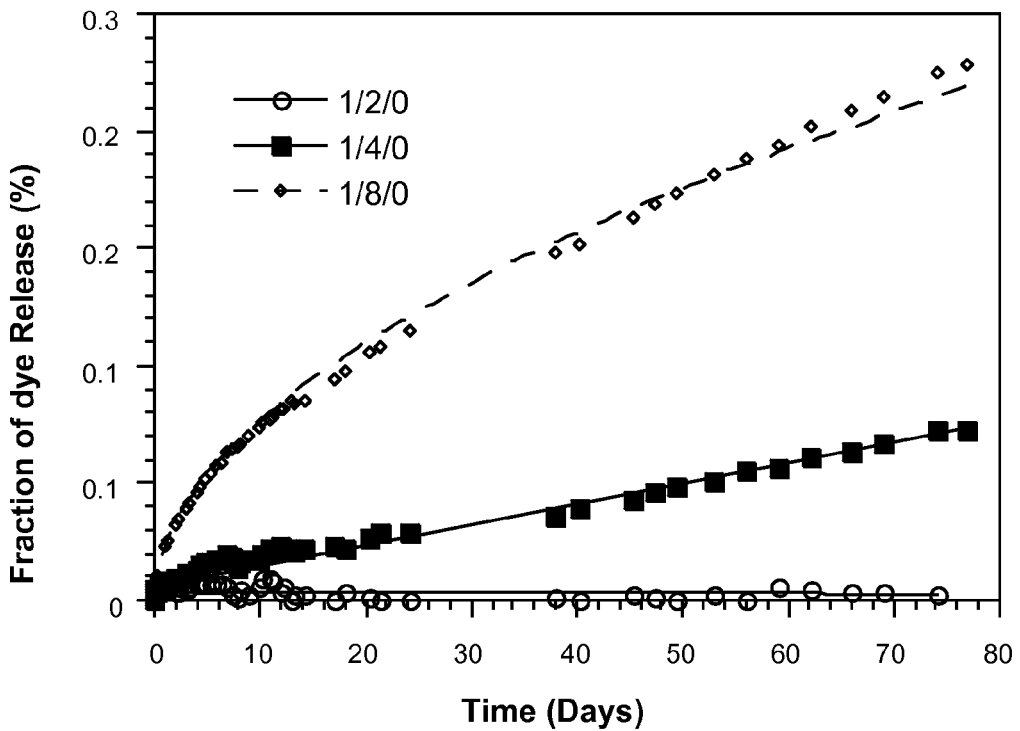

FIG. 2-1: Influence of the pH on the release for gels synthesised with W=4 and D=4. Acid region
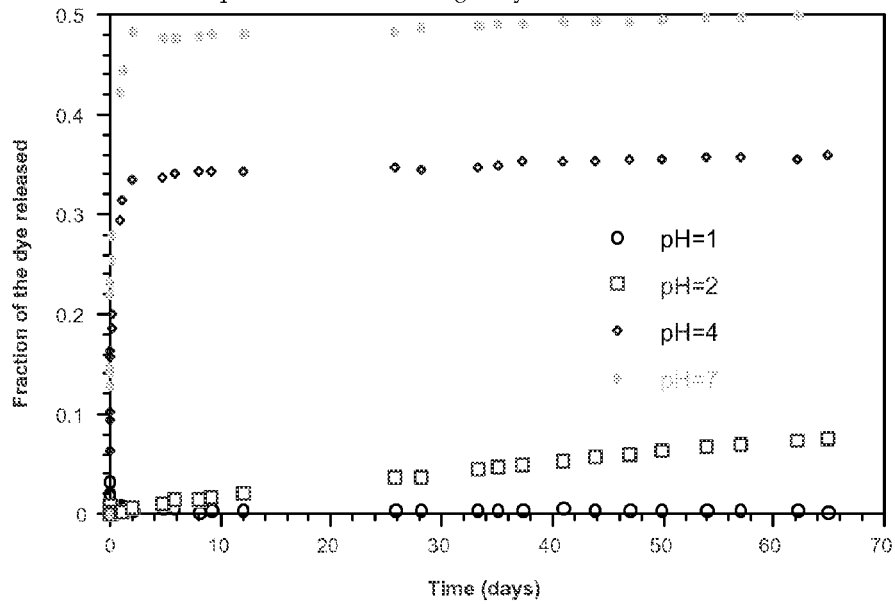
FIG. 2-2: Influence of the pH on the release for gels synthesised with W=4 and D=4. Basic region.
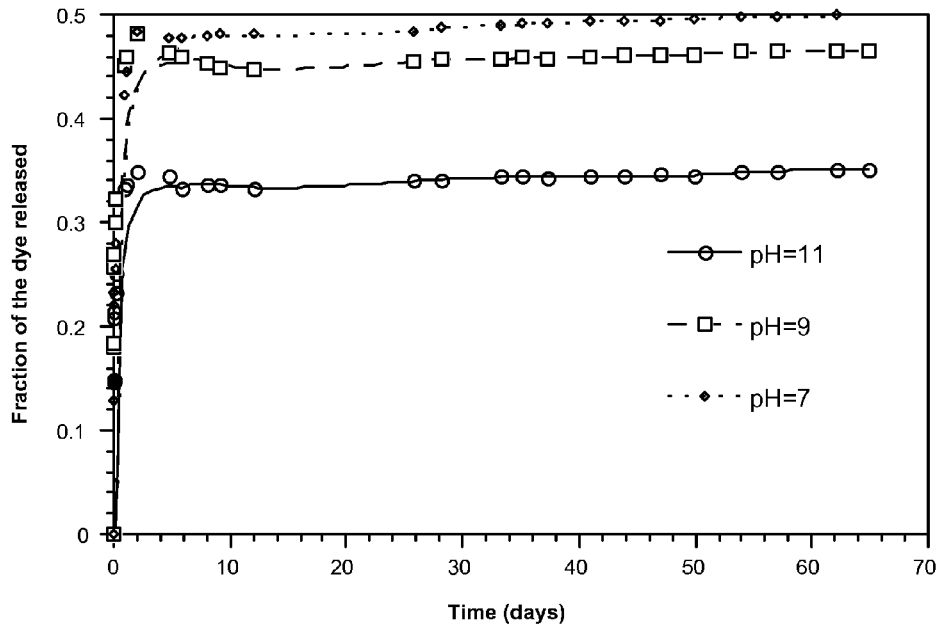

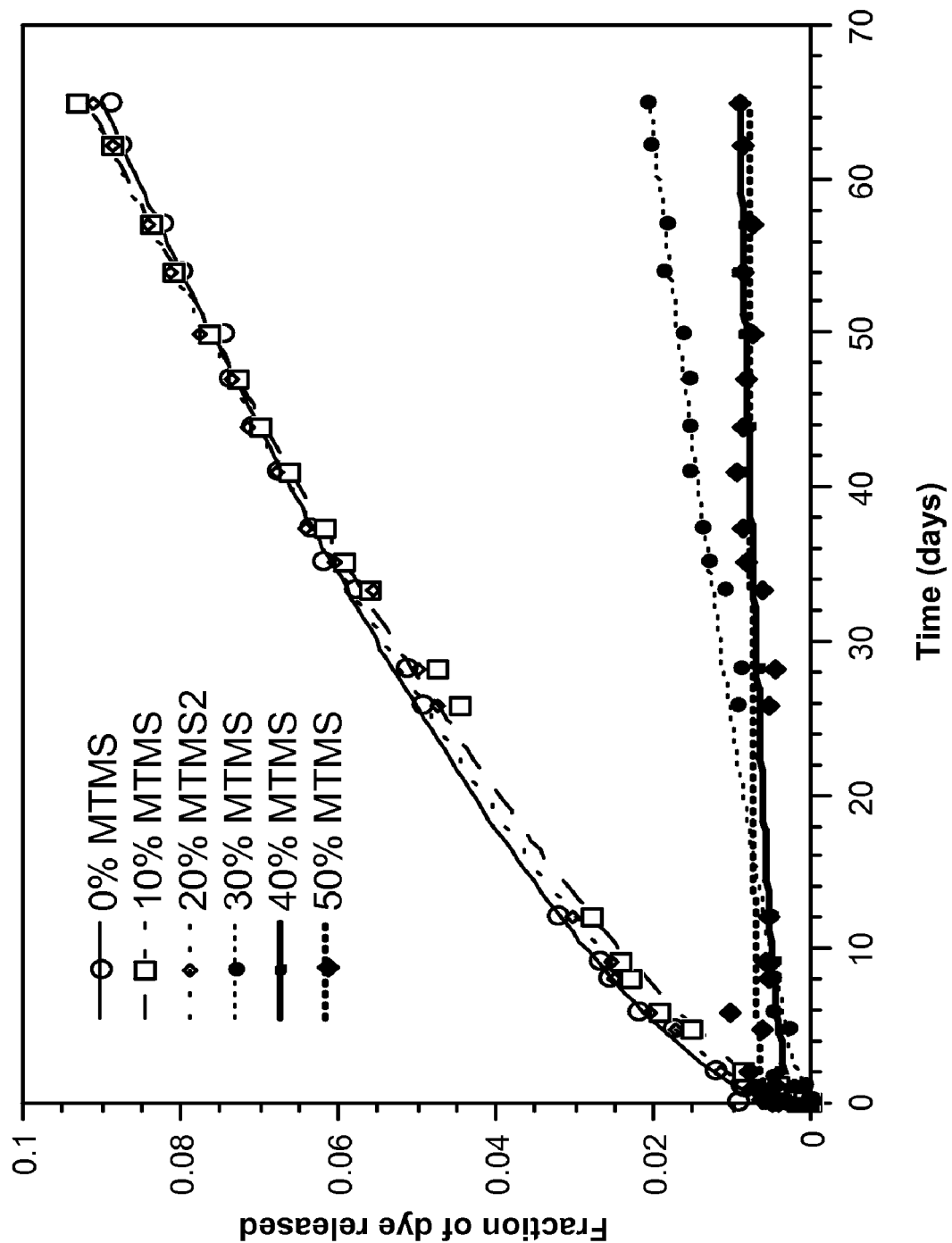
FIG. 3: Influence of MTMS substitution on the release rate

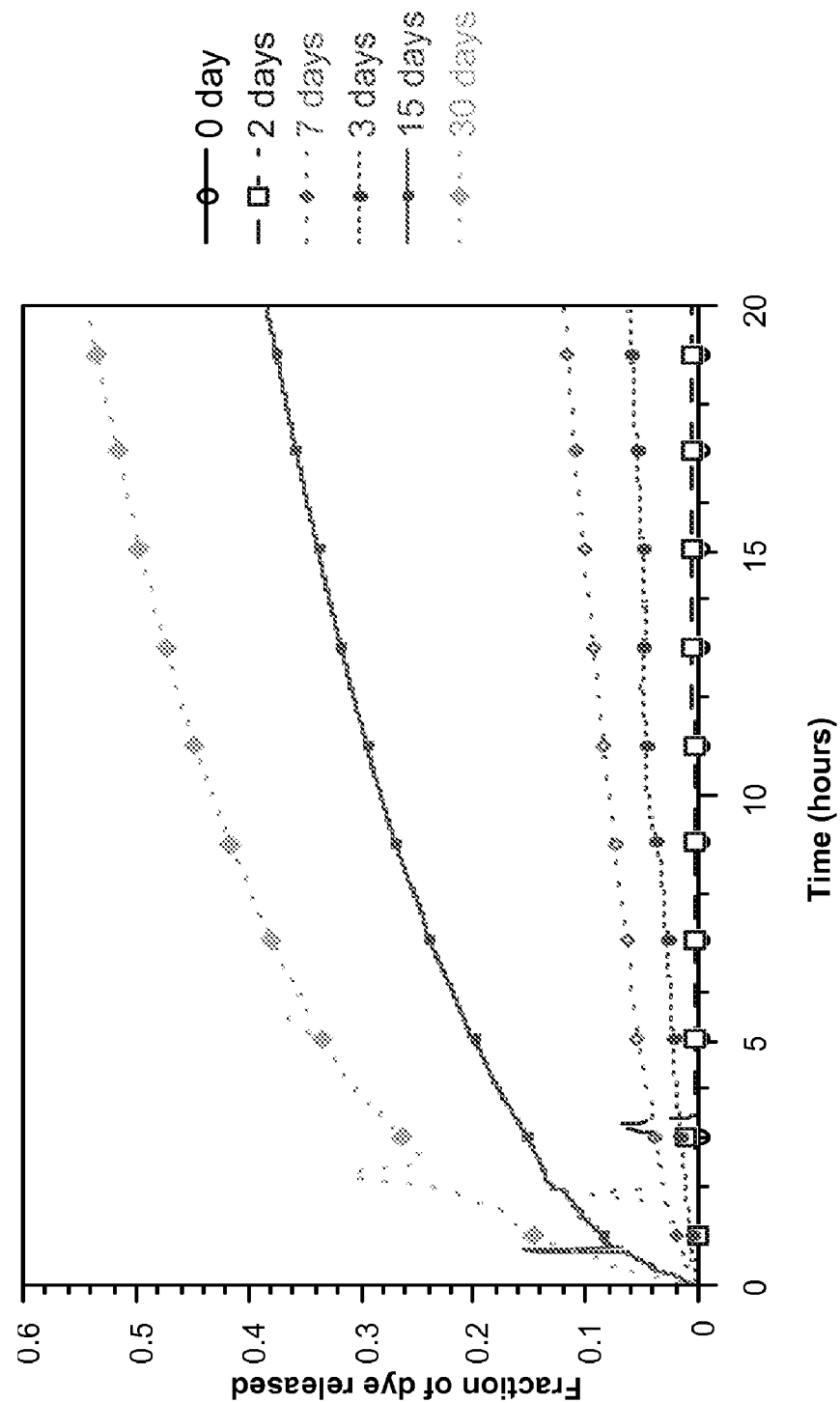
FIG. 4: Influence of the syneresis time on the release of Orange II

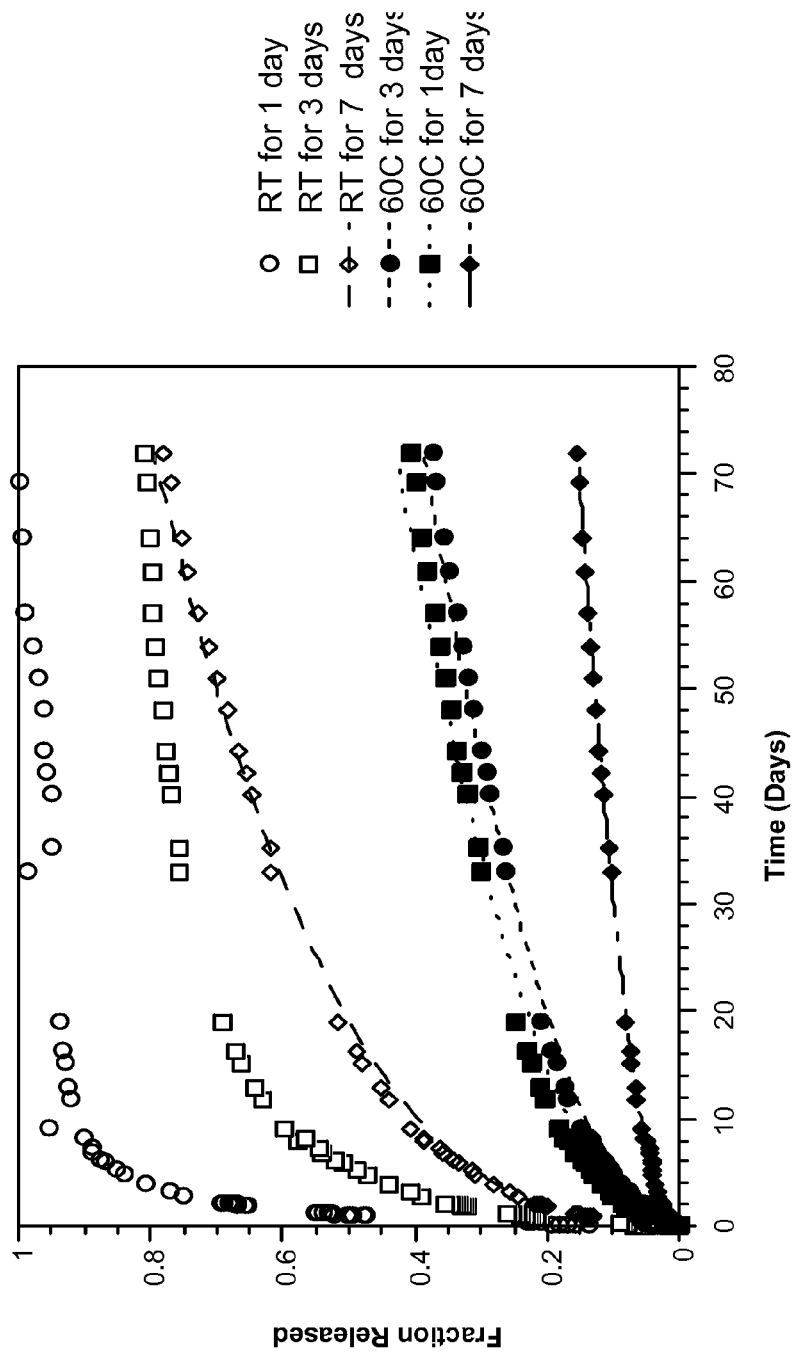
FIG. 5: Influence of the drying on the release from a gel synthesised with W=4 and D=0.

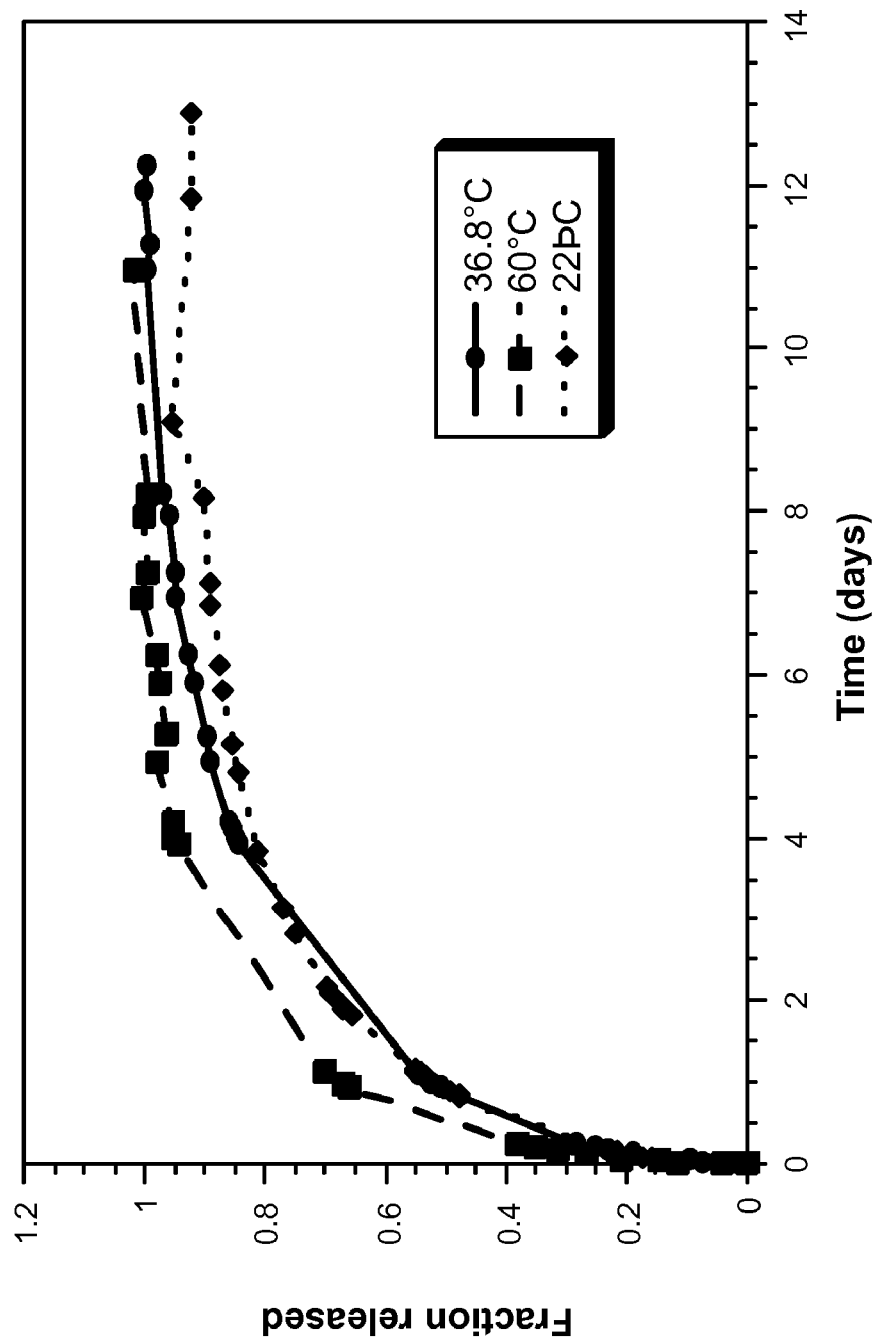
FIG. 7: Influence of the temperature of the release media on the release rate.

FIG. 8: Comparison of the release of gels containing Orange II and Methyl violet.
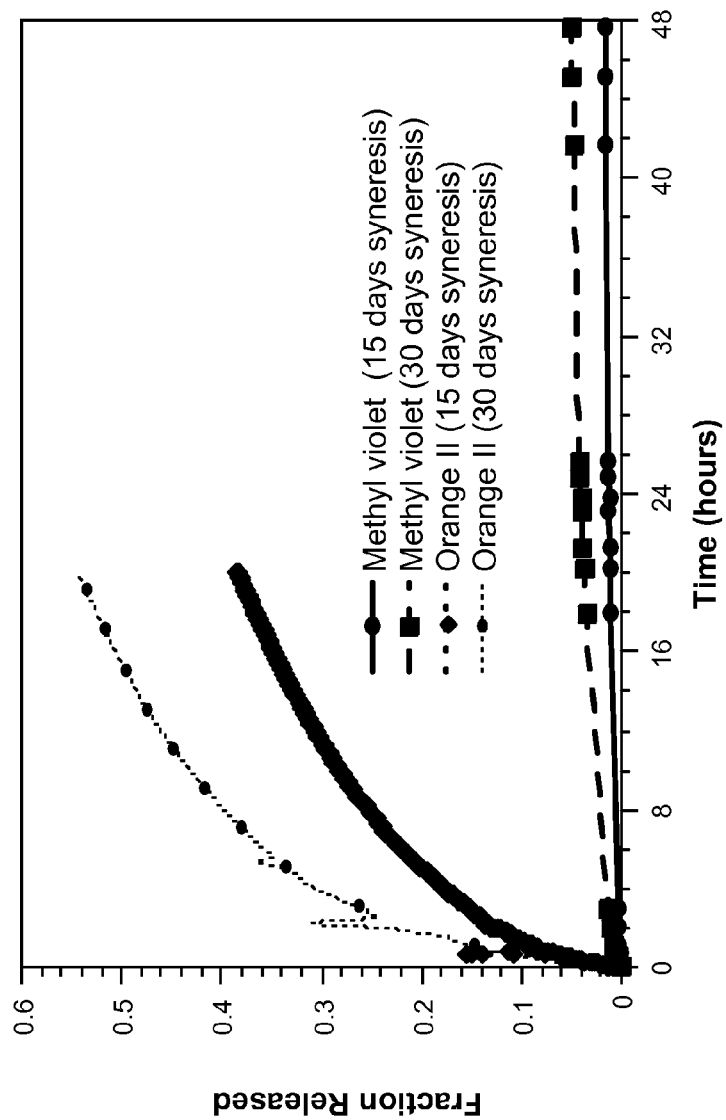

FIG. 9: Microspheres synthesised using a) heptane, b) octane c) dodecane and d) cyclohexane.
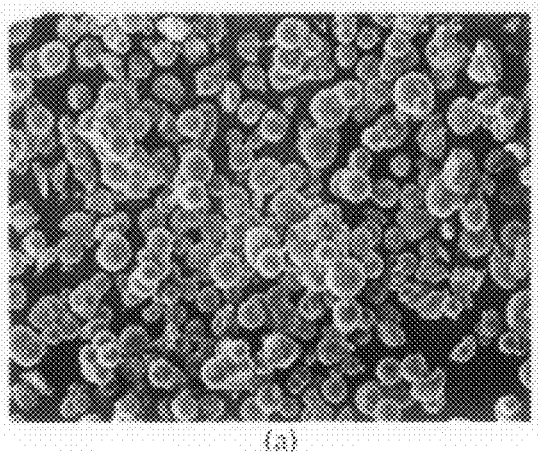
(a)
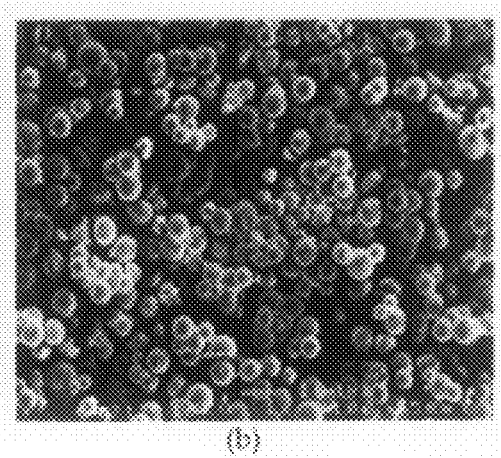
(b)
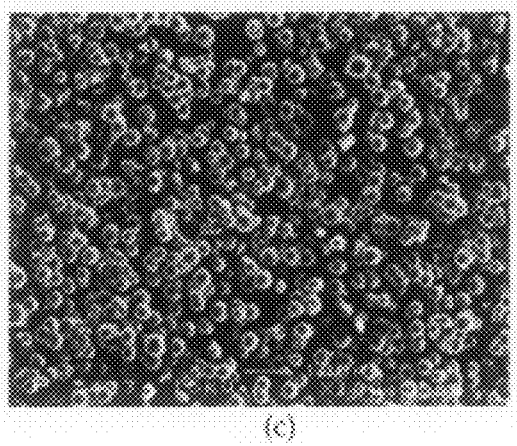
(c)
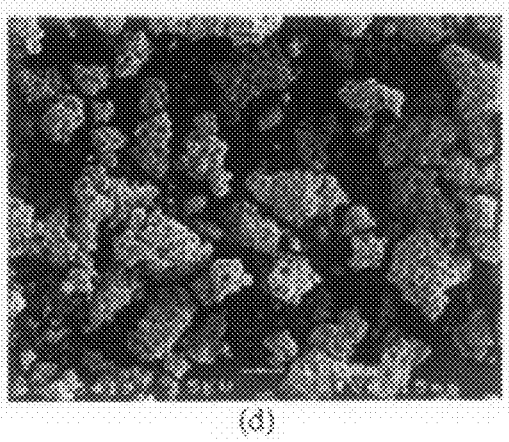
(d)

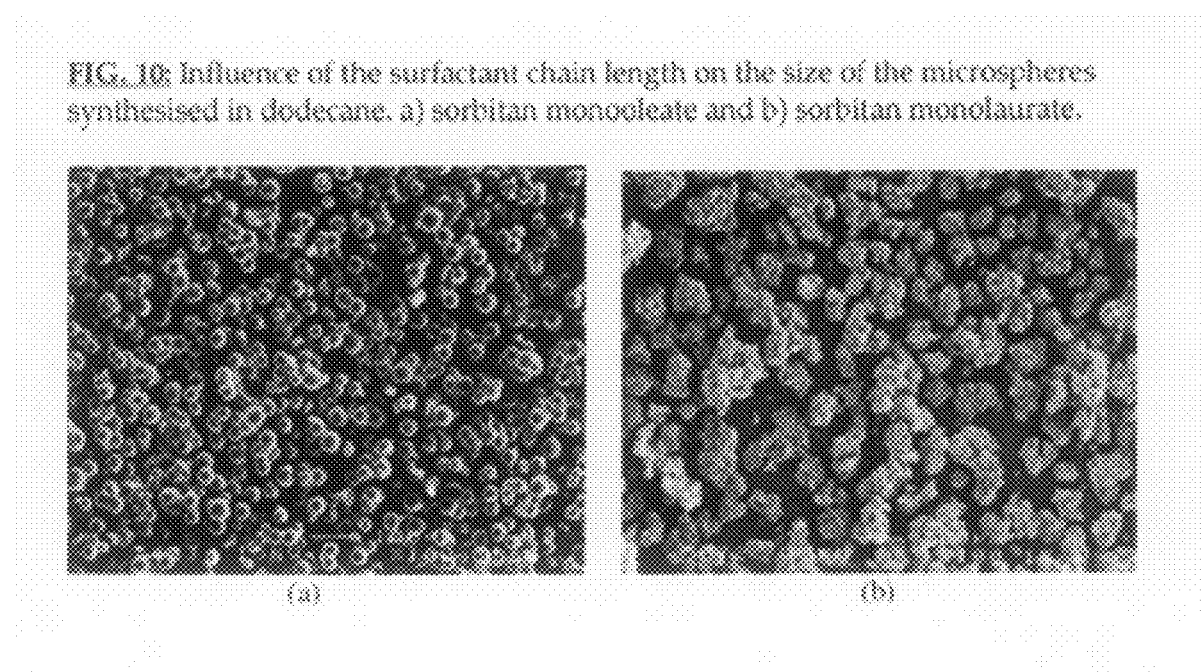
FIG. 10: Influence of the surfactant chain length on the size of the microspheres synthesised in dodecane. a) sorbitan monooleate and b) sorbitan monolaurate.

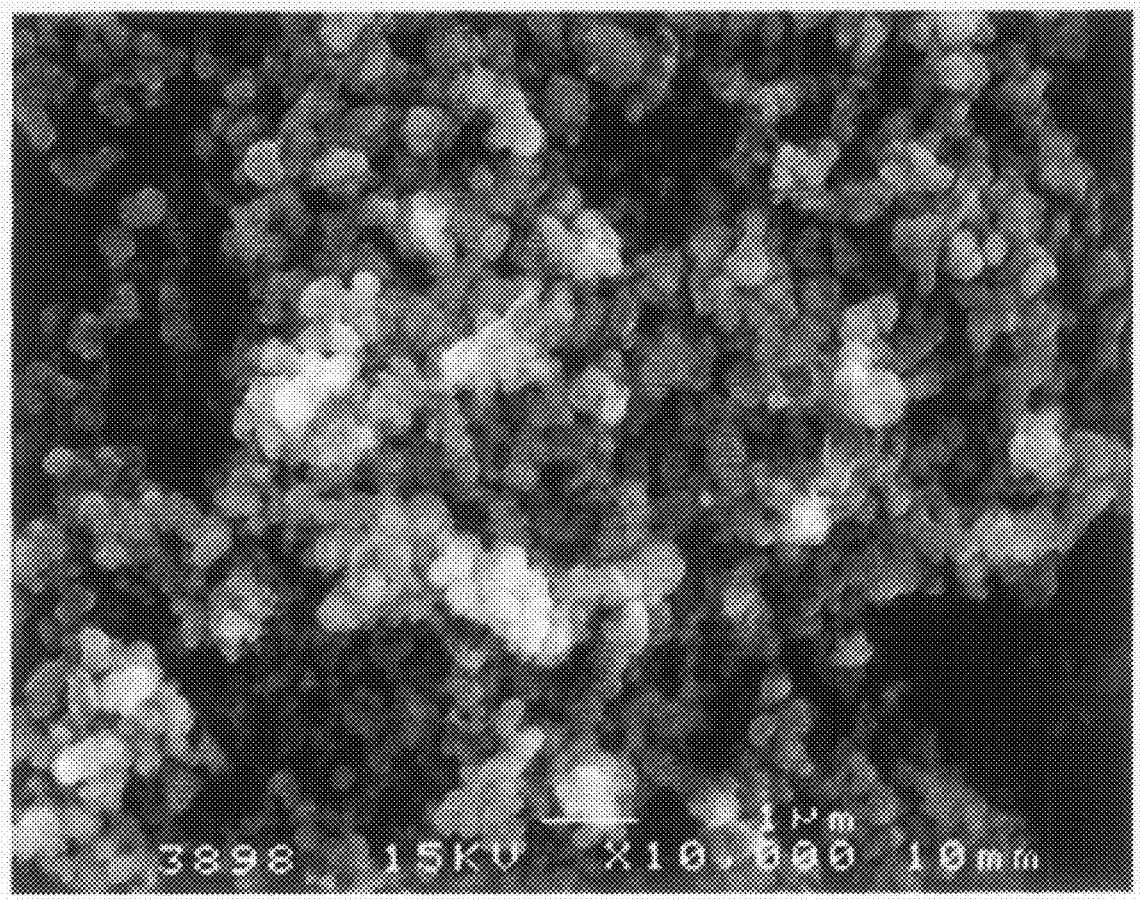
FIG. 11: SEM micrograph of nanospheres synthesised using an AOT/cyclohexane emulsion

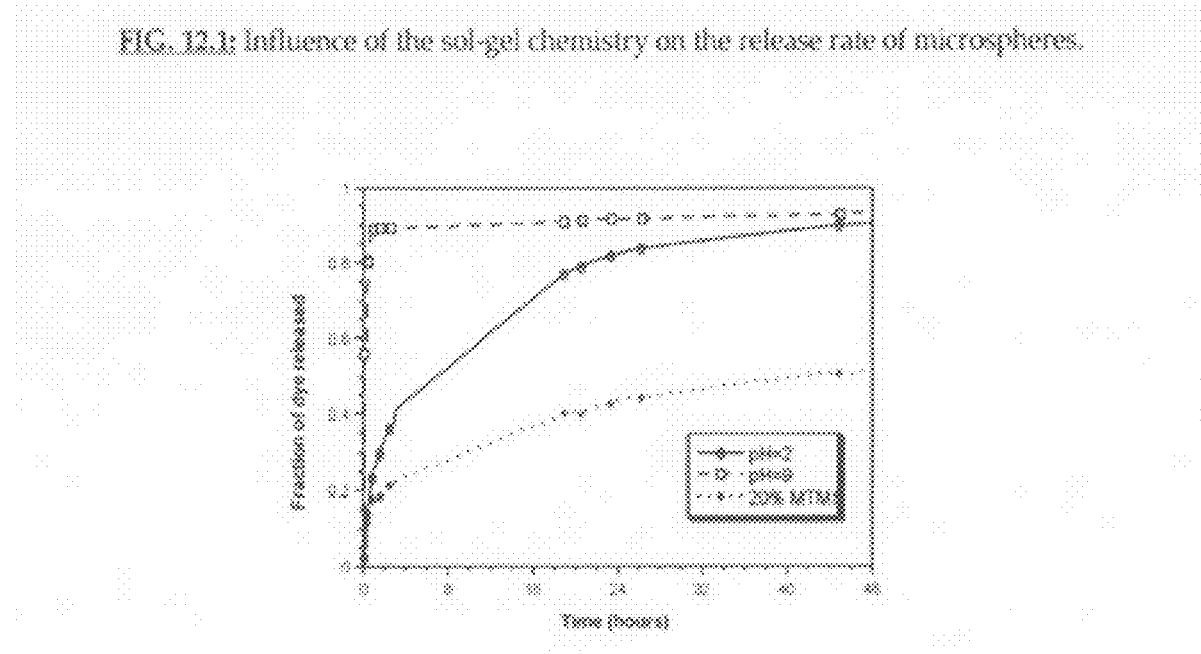
FIG. 12.1: Influence of the sol-gel chemistry on the release rate of microspheres.
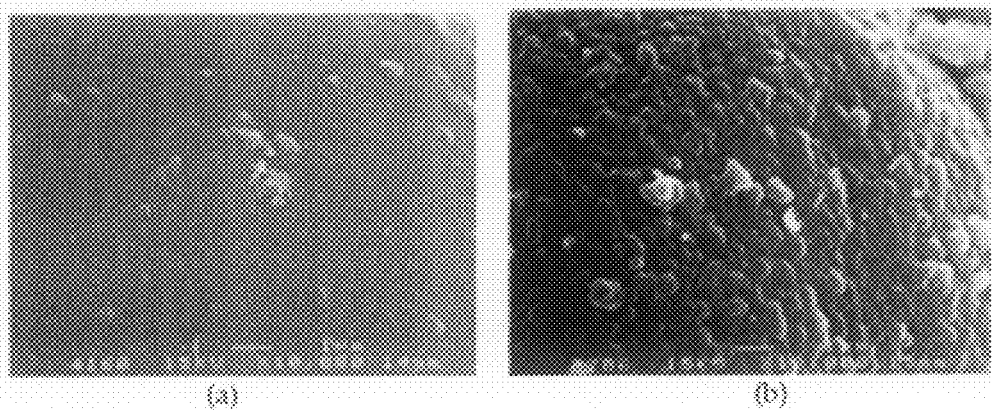
FIG. 12-2: SEM micrographs of the surface of microspheres synthesised from sol-gel solutions at pH=2 and pH=9.
(a)          (b)

FIG. 13: Influence of the drying temperature of microspheres on their release kinetics.
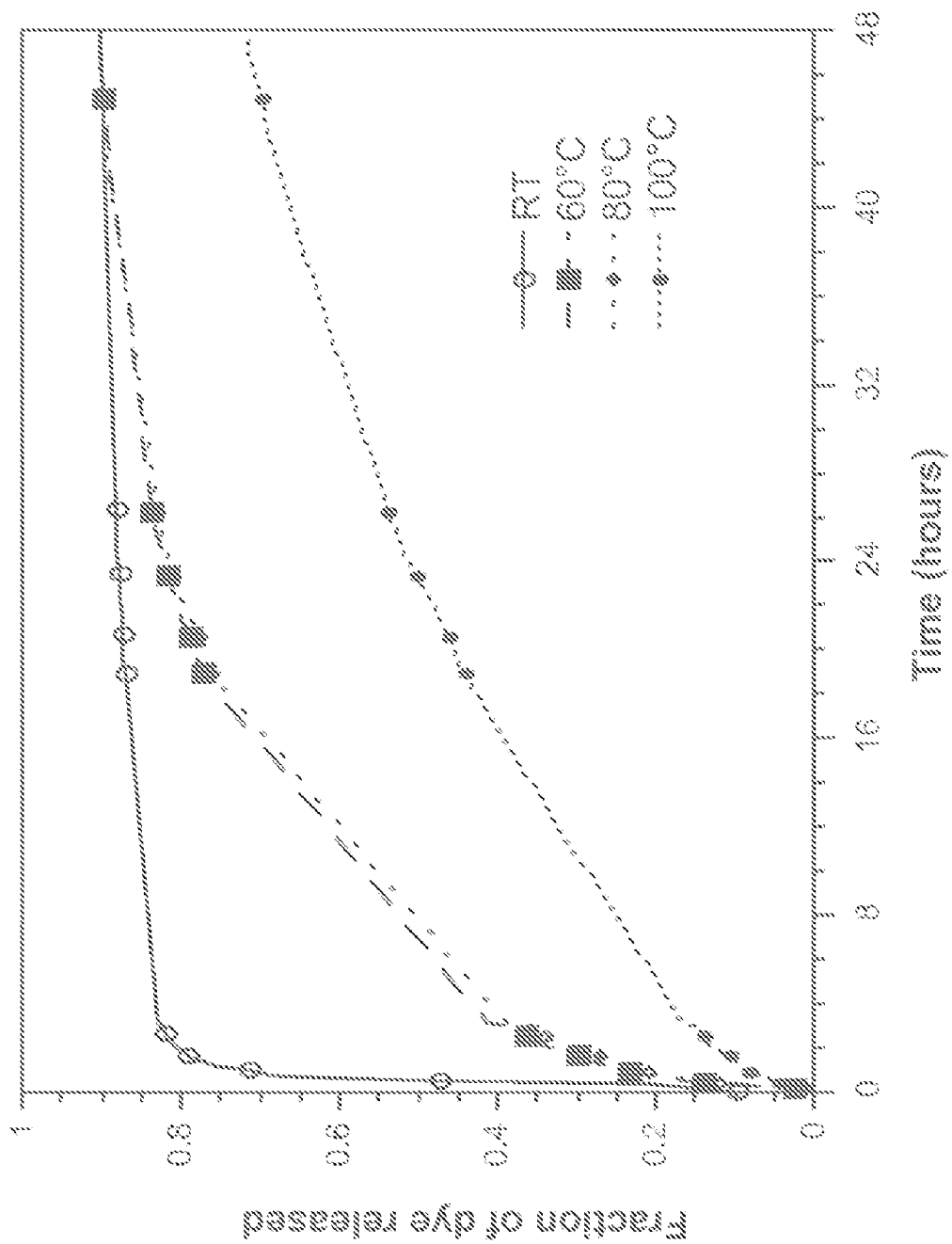

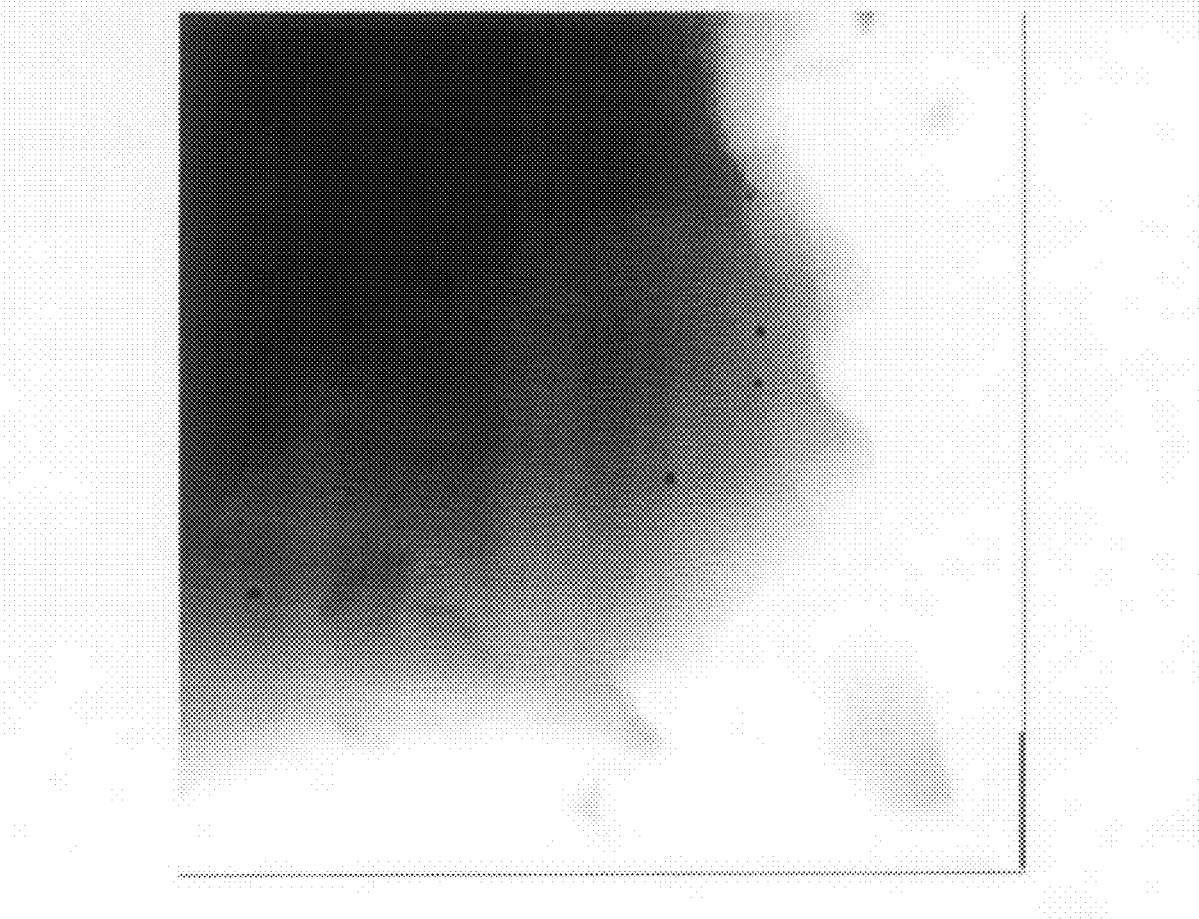
FIG. 14: TEM micrograph showing the precipitation of platinum colloids in the aged TMOS derived gel containing cis-platin.

FIG. 15-1: Influence of the incorporation of MTMS on the release rate of cycloheximide.
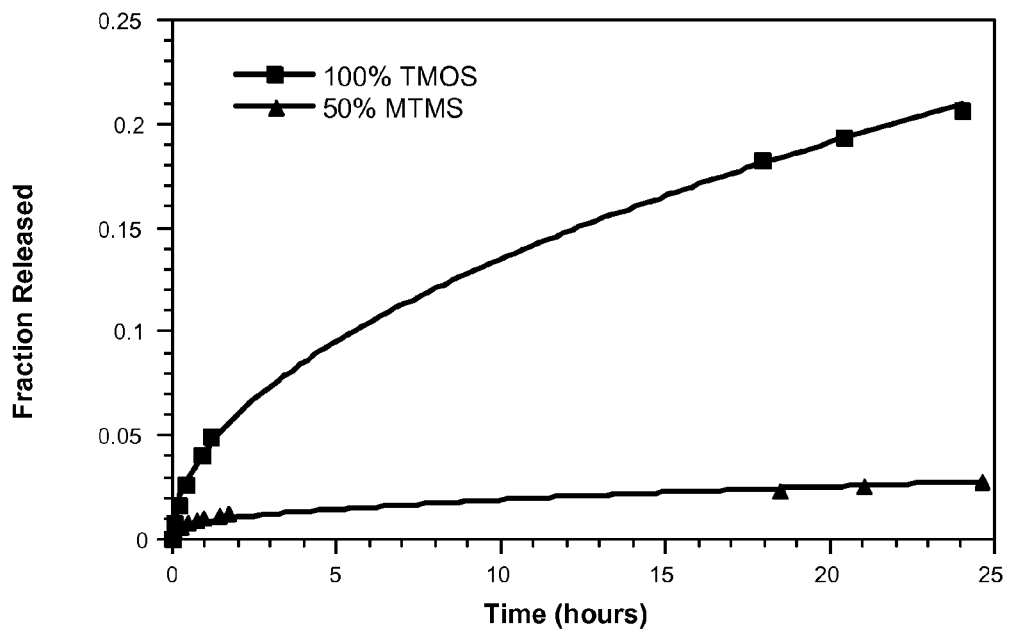
FIG. 15-2: Influence of the incorporation of MTMS on the release rate of cis-platin.
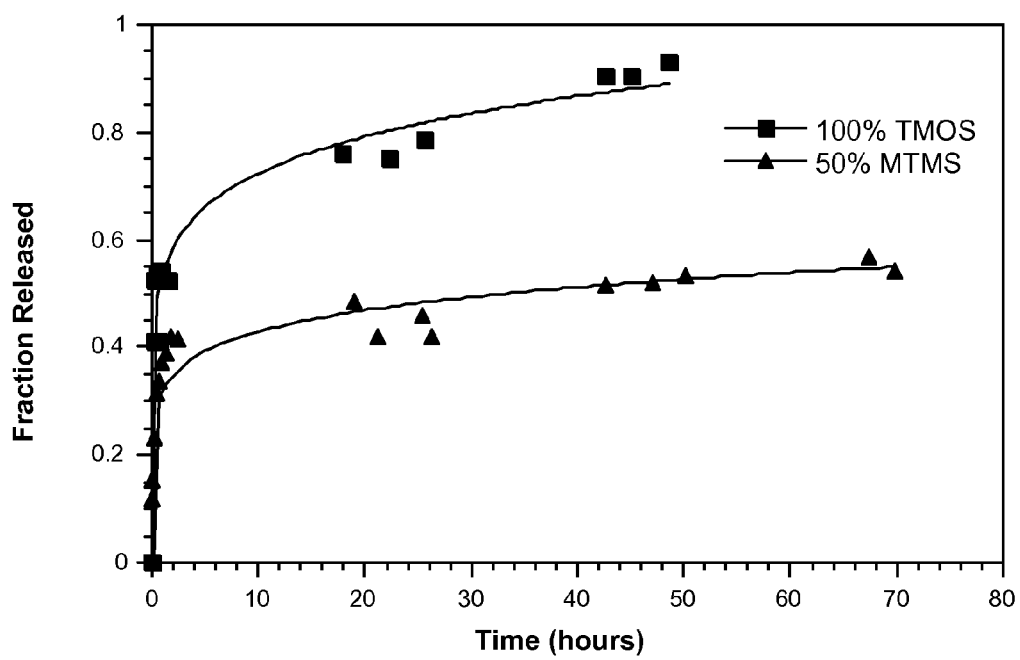

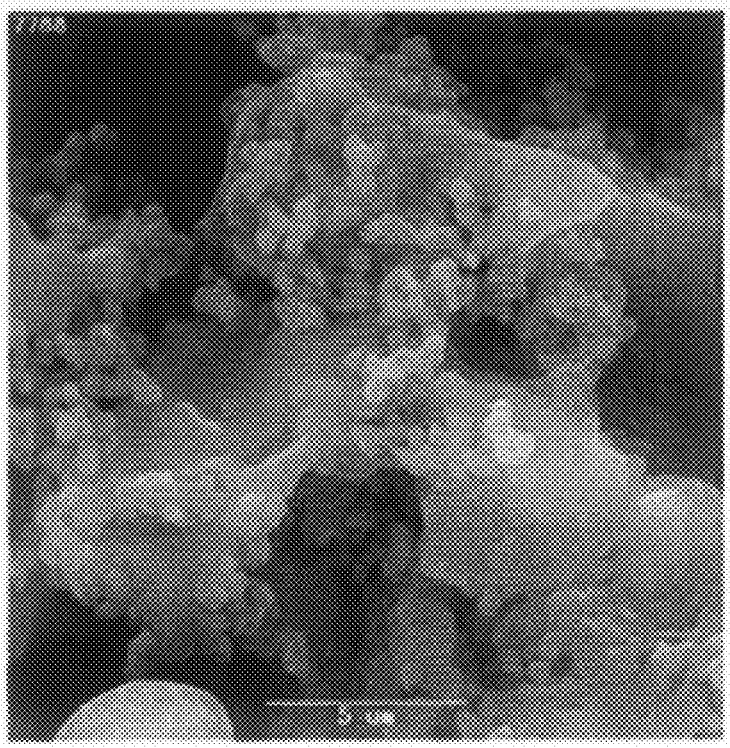
FIG. 17-1: SEM micrograph of Freeze-dried Cu doped nanoparticles encased in a gangue of NaCl

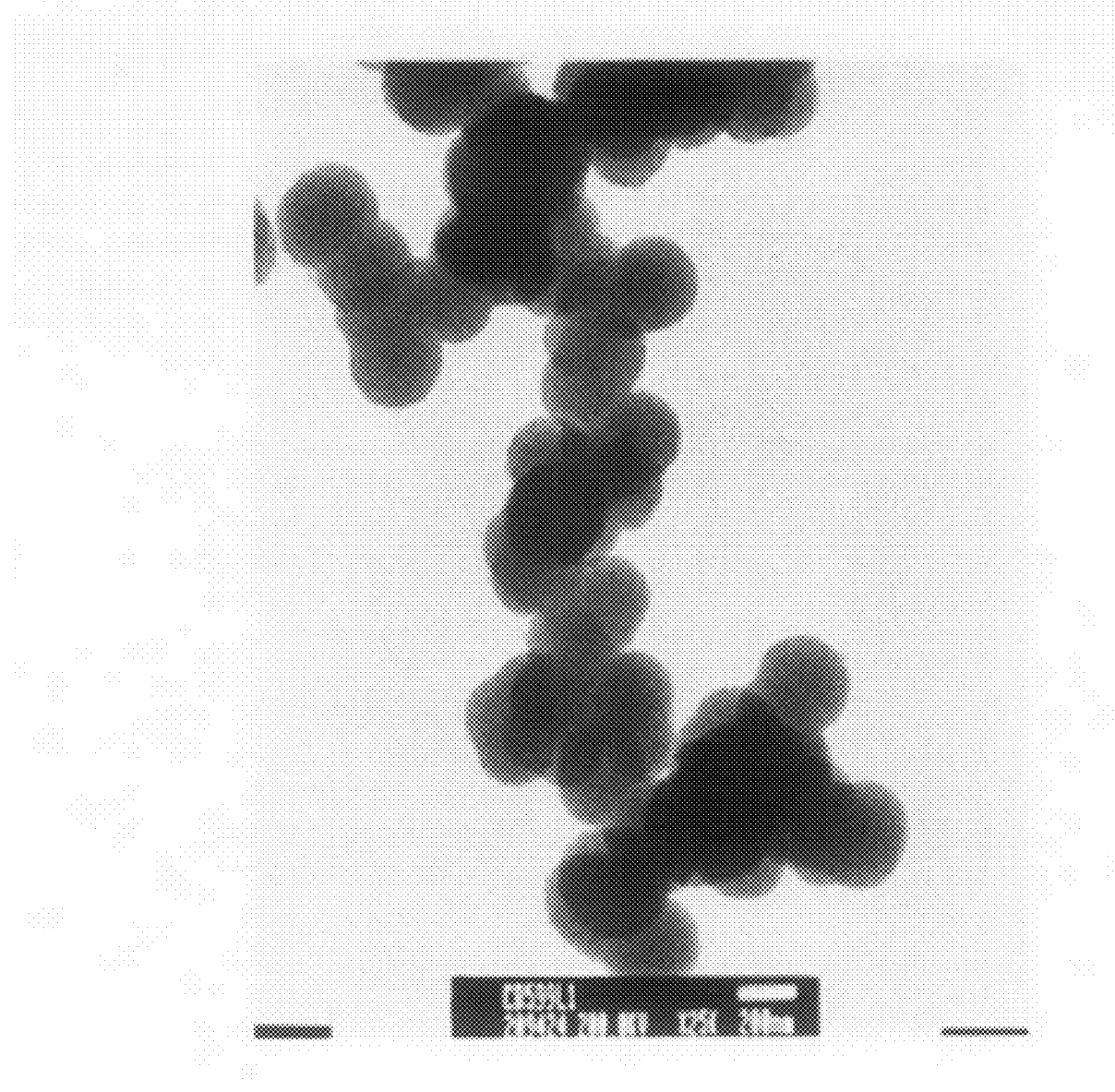
FIG. 17-2: TEM micrograph of the dialysed suspension.

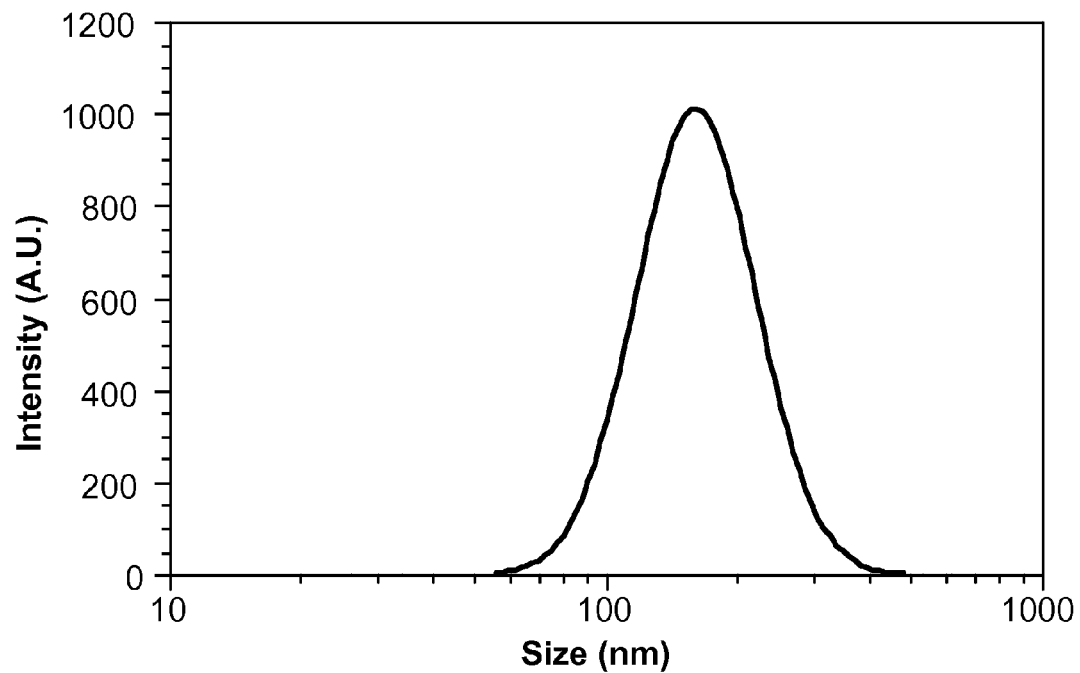
FIG. 17-3: Particle size distribution measured by photon correlation spectroscopy (PCS) of the freeze dried powder redispersed in water FIG. 18-1: TEM of the particle synthesised from a NP9/cyclohexane emulsion
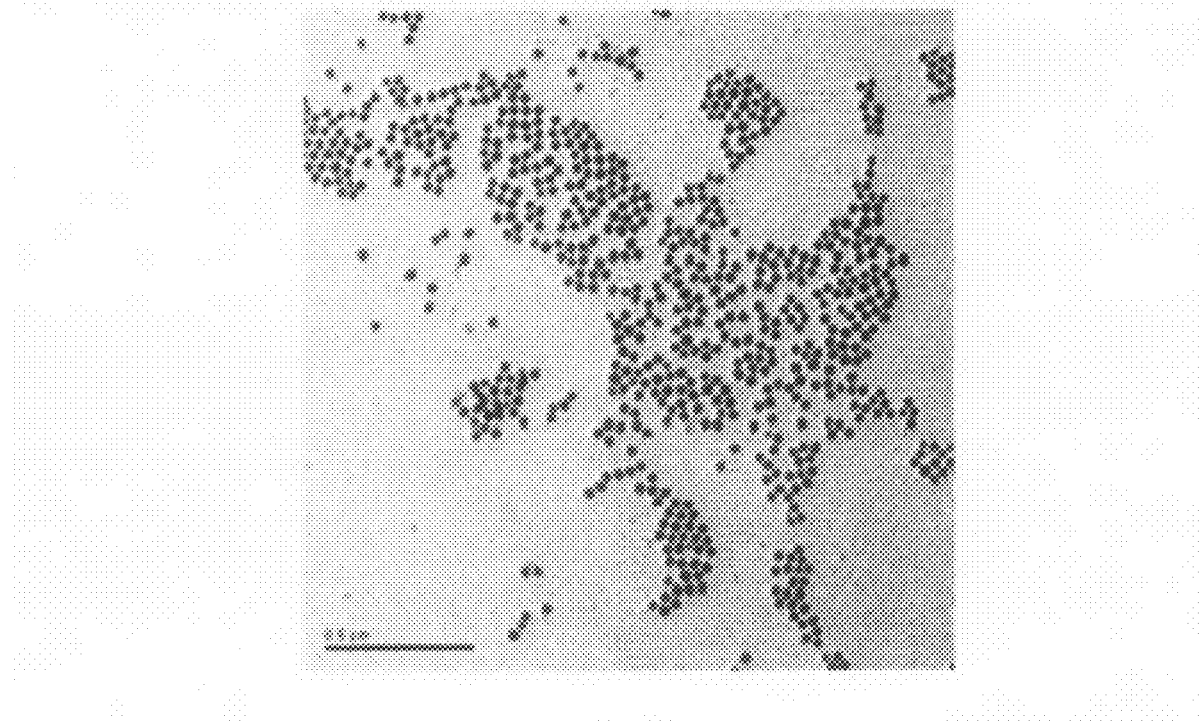
FIG. 18-2: Particle size distribution measured by photon correlation spectroscopy (PCS) of the particles synthesised from a NP9/cyclohexane emulsion.
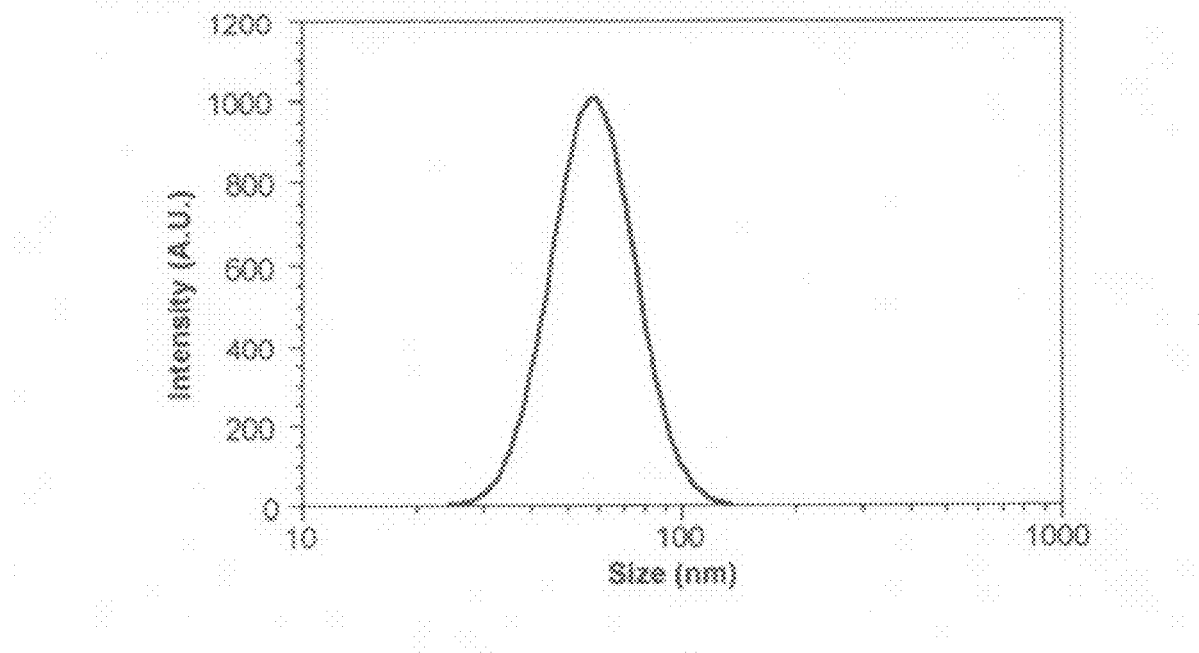

FIG. 19: SEM micrographs of Cu-doped particles synthesized with (a) S=2 and (b) S=10.
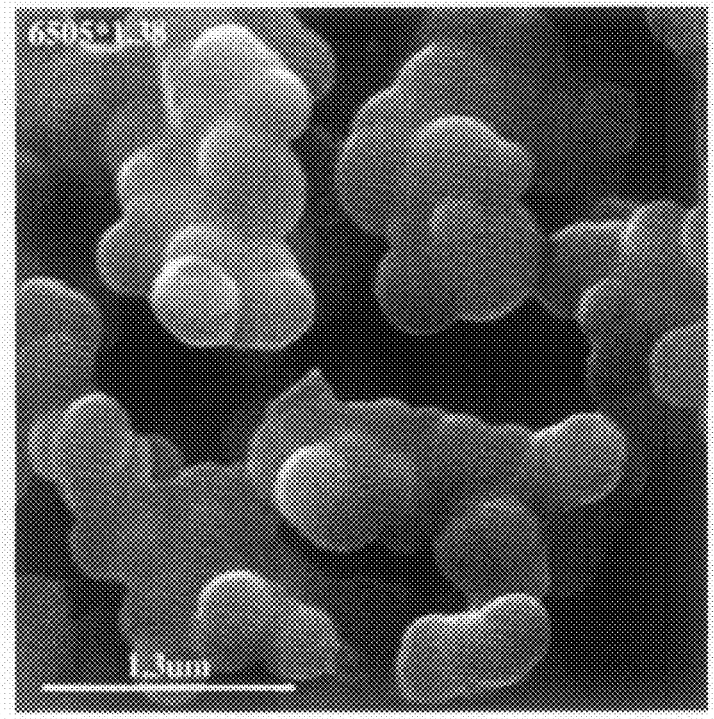
(a)
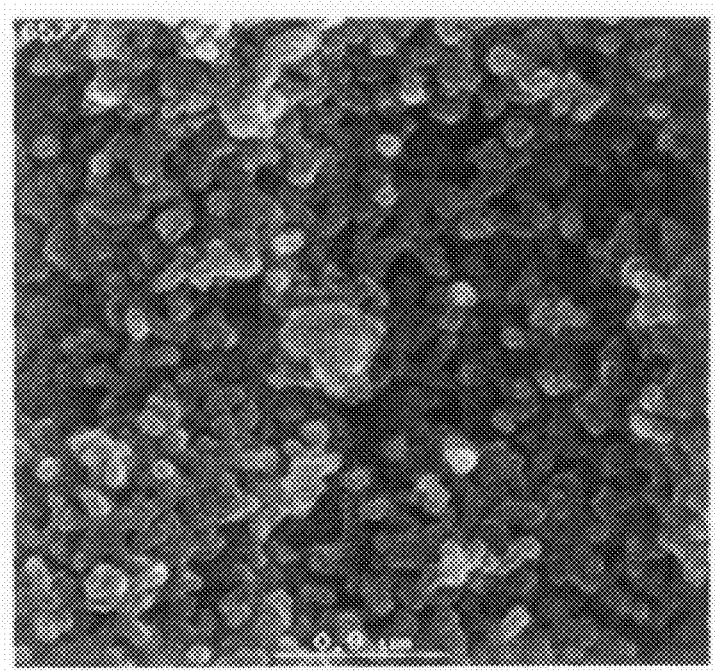
(b)

FIG. 20: Particle size distribution measured by PCS of the particles synthesised with W=88 and W=16.
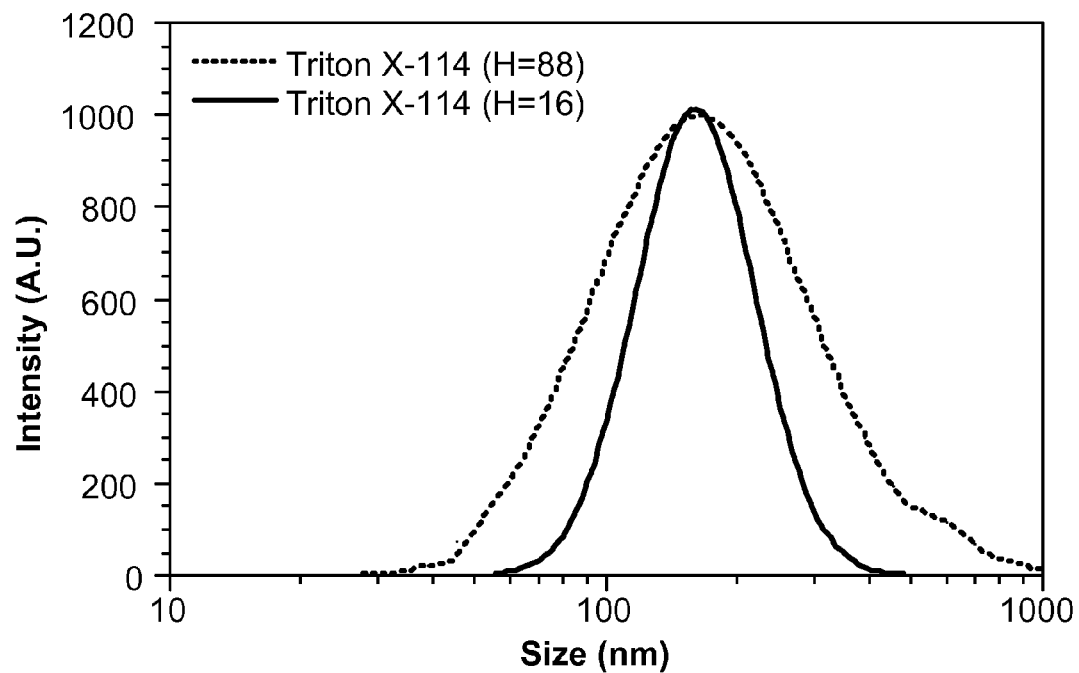

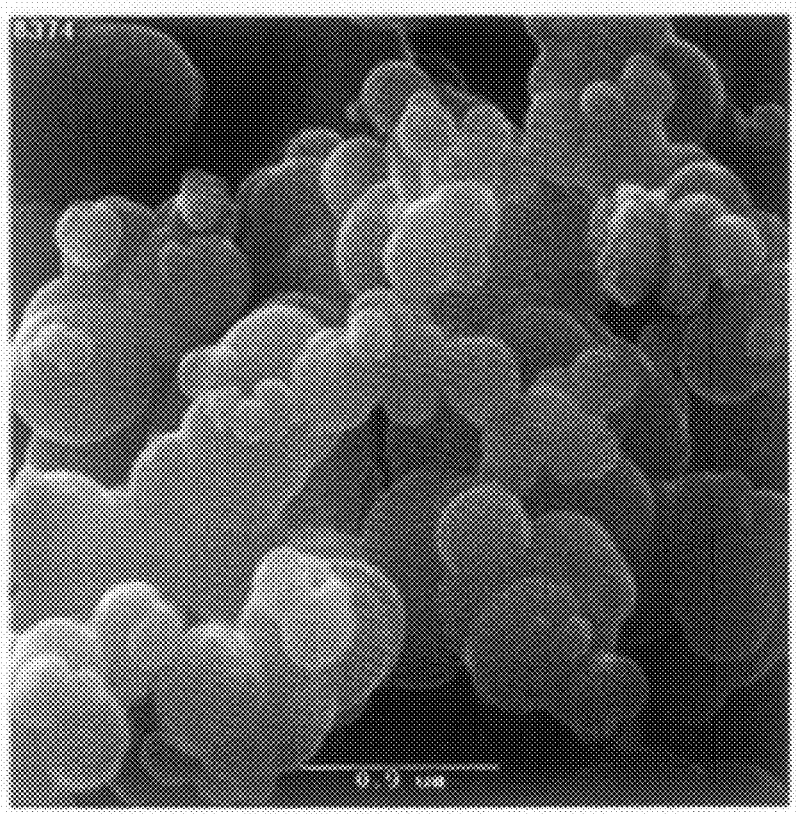
FIG. 21: SEM of particles synthesised by spontaneous emulsification (process 3)

FIG. 22: SEM micrographs of mixed oxide particles containing orange II and synthesised using process 1
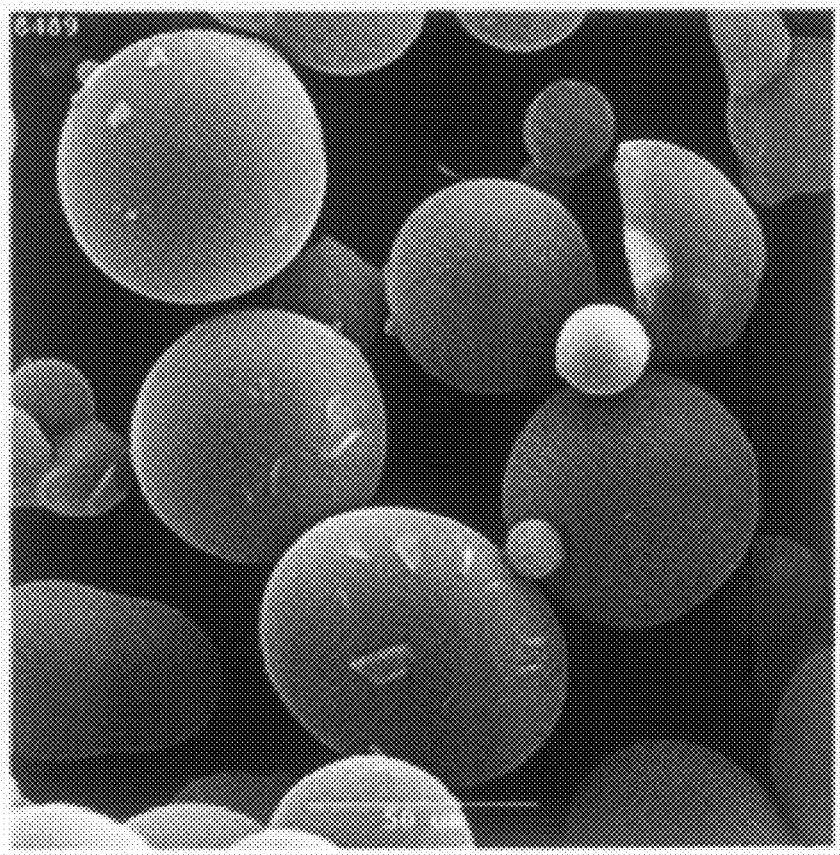

FIG. 23: Block Diagram showing a preferred process 4 of the invention
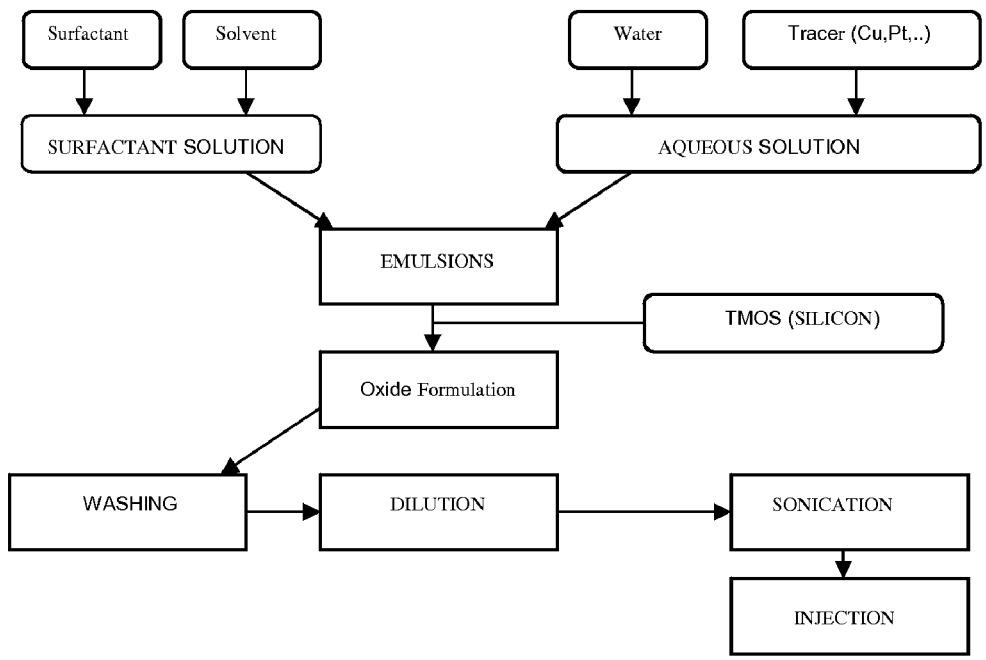
FIG. 24: Block Diagram showing a preferred washing procedure in relation to process 4 of the invention
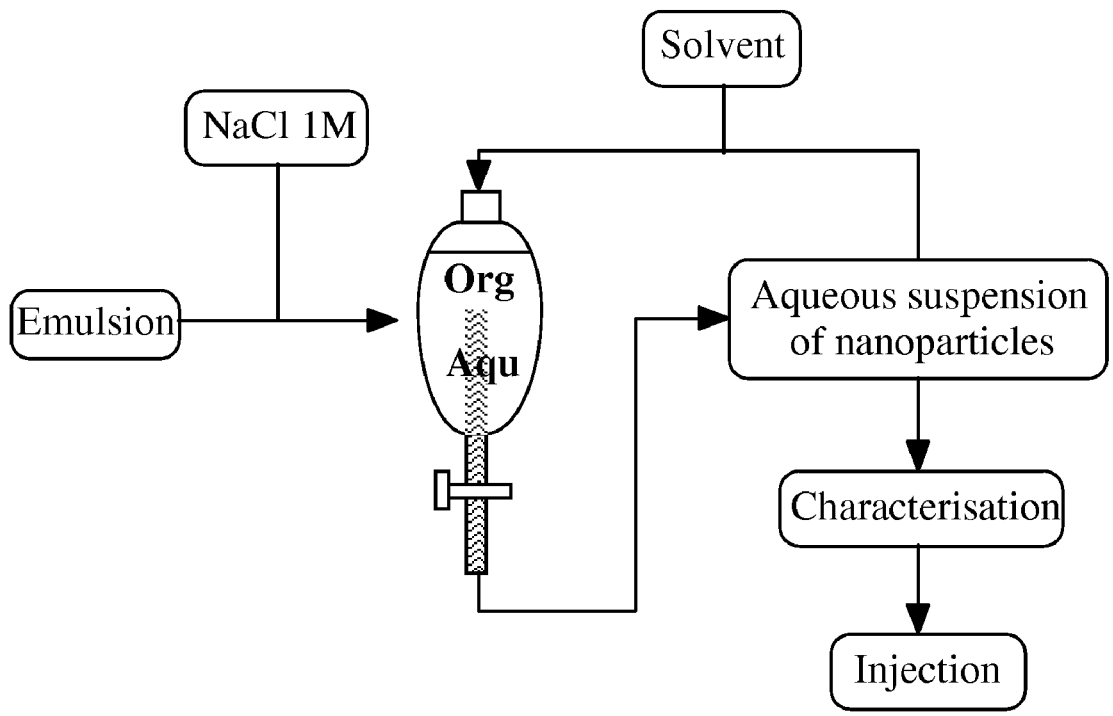

CONTROLLED RELEASE CERAMIC PARTICLES, COMPOSITIONS THEREOF, PROCESSES OF PREPARATION AND METHODS OF USE

CROSS-REFERENCE TO RELATED PATENT APPLICATIONS

This application is a Continuation of U.S. application Ser. No. 10/204,462 filed Nov. 22, 2002, now U.S Pat. No. 7,258,874, which is a National Stage of PCT/AU01/000173 filed Feb. 21, 2001, which claims priority to Australian Application PQ5733 filed Feb. 21, 2000, all of which are incorporated herein by reference in their entirety.

TECHNICAL FIELD

This invention relates to controlled release ceramic particles, substantially monodispersed controlled release ceramic particles, processes for preparing substantially monodispersed controlled release ceramic particles, substantially monodispersed controlled release ceramic particles prepared by such processes, compositions comprising controlled release ceramic particles according to the invention and methods of using controlled release ceramic particles according to the invention.

BACKGROUND ART

Current strategies for drug encapsulation and controlled release typically use organic vehicles such as polymers, liposomes and micelles.

(a) Polymeric systems can be broadly classified as:

Inert Matrix systems where the drug is trapped inside an inert, non-degradable polymer matrix, and its release controlled by diffusion through the porous network. In-vivo administration of such non-biodegradable polymeric particles is limited by the fact that the polymers will concentrate in intracellular "pockets" (e.g. lysosomes) or tissue, inducing severe overload of non-metabolised material. This limits their use to trans-dermal patches, etc. Another significant limitation is that the release is non-specific, since it is not activated by specific sites within the body. Finally, drug molecules exhibit intrinsically small diffusion coefficients within such matrices, limiting their broad application to potent drugs.

Reservoir systems, where the active ingredient's release is controlled by diffusion through an encapsulating membrane, hollow fibre, etc. The key limitations of these systems are their low mechanical strength and chemical resistance, since the controlling membrane is relatively fragile and easily fouled.

Chemical systems, in which the active molecules are dispersed inside a biodegradable matrix (e.g. polymers such as polyorthoesters and polyanhydrides). The release rate is preferably controlled by the heterogeneous (surface) dissolution/degradation of the matrix. This restricts the range of polymers that can be employed as matrices to bioerodible polymers such as poly(glycolic acid), poly(DL) lactic acid, poly(glycolic-colactic acid), poly caprolactone, polyhydroxy butyrate, and poly dioxianone.

Solvent-activated systems (hydrogels), in which the matrix swells in the presence of specific solute/solvent systems, with subsequent release of the encapsulated species. However, such polymers often swell too rapidly to provide therapeutically useful release rates, and the development of these systems is still in its infancy. In such controlled delivery systems, the delivery is controlled either by matrix structure (e.g. pore network tortuosity), particle size, overall drug loading or matrix solubility. A limitation of polymeric systems is that they can typically only exploit one, or at most two, of these features, and any changes in the drug usually necessitates reformulation of the matrix system. In contrast, an important feature of the present invention is that all of these features can be manipulated using the same underlying chemistry, which provides a more generic approach to designing controlled release matrices for specific applications.

Moreover, while there are many polymeric materials that have been identified as having potential for controlled drug release, relatively few have been approved for use in either human or veterinary pharmaceutical products.

(b) Liposomes are the most highly developed carrier system, but suffer from problems with in-vivo stability, aging and limited shelf life.

(c) The thermodynamic instability of micelles (which depends on temperature, concentration, solution speciation, etc) limits their applicability for controlling release. They also exhibit intrinsically low drug loading (d) Bioceramics are used in bone-repair procedures (inert bioceramics, porous active ceramics that promote osteo-reconstruction). The inert bioceramics have purely mechanical applications, e.g. hip-joints (because of their low coefficient of friction)-typically $Al_2O_3$ or Y-TZP. The porous ceramics (typically hydroxy apatites) serve as structural bridges and "scaffolds" for bone formation. Bioactive glass provides an interfacial layer for tissues growth that resists substantial mechanical forces. Bioactive glasses have also been proposed as matrices for the controlled delivery of bioactive substances.

Various patents have been issued to matrices prepared by sol-gel based processes, for example:

U.S. Pat. No. 5,591,453 (awarded Sep. 1, 1997) discloses the use of sol-gel silica matrices for the controlled release of biologically active molecules. The application cited was for osteo-reconstruction, and was restricted to large gel monoliths or granules (typically 0.5 to 5 mm). The release is controlled either by drug loading or varying the surface to volume ratio. Possible interactions between the matrix and drug were ignored. British Patent 1 590 574 (awarded Mar. 6, 1981) discloses the concept of incorporating biologically active components in a sol-gel matrix. Embodiment as substantially spherical particles in the size range from several microns to several millimetres was envisaged. It was noted that the rate of release of the biologically active component from the matrix would depend on a number of factors, including the pH of the medium, size of particles, and composition/porosity/structure/water content/hydrophilicity of the gel. The only example given was of spray-dried particles produced from bohemite sols, from which all of the imipramine initially encapsulated was released within five minutes. WO 9745367 (issued Apr. 12, 1997) discloses controllably dissolvable silica xerogels prepared via a sol-gel process, into which a biologically active agent is incorporated by impregnation into pre-sintered particles (1 to 500 µm) or disks. The release was controlled by varying the dimensions and chemical composition of the xerogels. WO 0050349 (issued 31 Aug. 2000) discloses controllably biodegradable silica fibres prepared via a sol-gel process, into which a biologically active agent is incorporated during synthesis of the fibre. The release was primarily controlled by varying the dissolution rate of the fibres.

OBJECTS OF INVENTION

Objects of the invention are to provide controlled release ceramic particles, substantially monodispersed controlled release ceramic particles, processes of preparing substantially monodispersed controlled release ceramic particles, substantially monodispersed controlled release ceramic particles prepared by such processes, compositions comprising such controlled release ceramic particles and methods of using such controlled release ceramic particles.

DESCRIPTION OF INVENTION

According to an embodiment of this invention there is provided controlled release ceramic particles, wherein each of said particles has an active material(s) substantially homogeneously dispersed throughout the particles and wherein the active material(s) is capable of being released from said particles.

The controlled release ceramic particles may be functionalised or derivatised.

According to another embodiment of this invention there is provided controlled release ceramic particles, wherein each of said particles has an active material(s) substantially homogeneously dispersed throughout the particles, wherein:
  (a) the active material(s) is capable of being released from said particles; and
  (b) the active material(s) in said particles is substantially protected from degradation until release of the active material(s) from the particles.

In other words, in the above embodiment each of the particles has an active material substantially homogeneously dispersed throughout the particle wherein the active material is capable of being released from the particle and the active material in the particles is incorporated within the particles so as to be substantially protected from degradation until release of the active material from the particles.

During fabrication of the particles surfactant is typically removed from the particles so that they contain less than about 2 wt % surfactant, typically between 0.1-2 wt %, more typically 0.5-2 wt %, even more typically between 1-2 wt %.

Typically ceramic particles comprise an oxide selected from the group consisting of silica, zirconia, alumina and titania.

The controlled release ceramic particles of the invention may be advantageously prepared by a sol gel process.

The ceramic particles may be in the form of freeze dried particles or alternatively they may be dispersed in solution. Typically when the particles are in the form of freeze dried particles they are mixed with or in a matrix with an ionic salt.

According to one embodiment of this invention there is provided substantially monodispersed controlled release ceramic particles, wherein each of said particles has an active material(s) substantially homogeneously dispersed throughout the particles and wherein the active material(s) is capable of being released from said particles.

The substantially monodispersed controlled release ceramic particles may be functionalised.

The substantially monodispersed controlled release ceramic particles of the invention may be advantageously prepared by a sol gel process.

According to another embodiment of this invention there is provided substantially monodispersed controlled release ceramic particles, wherein each of said particles has an active material(s) substantially homogeneously dispersed throughout the particles, wherein:
  (c) the active material(s) is capable of being released from said particles; and
  (d) the active material(s) in said particles is substantially protected from degradation until release of the active material(s) from the particles.

The substantially monodispersed controlled release ceramic particles may be functionalised or derivatised.

The rate of release of the active material(s) from said particles is controlled by one or more of: the nature of the active material(s), particle properties and external environment.

When the active material(s) is released from the particles into an environment that does not substantially affect the activity of the active material(s), the activity of the active material(s) released from the particles is substantially retained.

Under usual conditions chosen for storage, transport, handling and in the environment of use the active material(s) in said particles is substantially protected from degradation until release of the active material(s) from the particles. An example of the usual conditions of storage, transport or handling includes storage, transport or handling of the particles in an environment that is non corrosive to the particles themselves. Also the usual conditions of storage, transport or handling do not normally include exposing the particles to an environment where degrading materials in the environment (such as a degrading gas or liquid) can enter the particles and degrade the active material(s) in the particles.

The invention also provides processes for making substantially monodispersed controlled release ceramic particles and particles made by such processes.

Process 1

According to one embodiment of the invention there is provided a process of preparing controlled release ceramic particles comprising:
  (a) preparing a reverse micelle solution by mixing a surfactant with an apolar solvent;
  (b) preparing a precursor solution by dissolving a gel precursor, a catalyst, a condensing agent and a (or several) soluble active material(s) in a polar solvent;
  (c) preparing an emulsion by combining the reverse micelle solution and the precursor solution; and
  (d) forming and aging controlled release ceramic particles, wherein each of said particles has the active material(s) substantially homogeneously dispersed throughout the particle and wherein the active material(s) is capable of being released from said particle, by condensing the precursor in the emulsion.

Usually the particles are substantially monodispersed.

Process 2

According to another embodiment of the invention there is provided a process of preparing controlled release ceramic particles comprising:
  (a') preparing a reverse micelle solution by mixing a surfactant with an apolar solvent and a hydrophilic first (or several) active material(s);
  (b') preparing a precursor solution by dissolving a gel precursor, a catalyst, a condensing agent and optionally a soluble second (or several) active material(s) in a polar solvent, which is immiscible with the apolar solvent used in (a);
  (c') preparing an emulsion by combining the reverse micelle solution and the precursor solution; and
  (d') forming and aging controlled release ceramic particles, wherein each of said particles has the active material(s) substantially homogeneously dispersed throughout the particle and wherein the active material(s) is capable of being released from each of said particles, by condensing the precursor in the emulsion.

Usually the particles are substantially monodispersed.

Process 3

According to a further embodiment of the invention there is provided a process of preparing controlled release ceramic particles comprising:
- (a") preparing a precursor solution by mixing a gel precursor, an (or several) active material(s) and optionally a solvent;
- (b") preparing a condensing solution by mixing a catalyst, a condensing agent and optionally a solvent, said condensing solution being substantially immiscible with said precursor solution;
- (c") combining the precursor solution and the condensing solution to form a mixture and preparing an emulsion by spontaneously emulsifying the mixture in the absence of a surfactant; and
- (d") forming and aging controlled release ceramic particles, wherein each of said particles has the active material(s) substantially homogeneously dispersed throughout the particle and wherein the active material(s) is capable of being released from each of said particles, by condensing the precursor in the emulsion.

Usually the particles are substantially monodispersed. In this embodiment the active material is one that can be dissolved in the gel precursor or in the gel precursor together with the solvent. In addition, the catalyst is one that can be dissolved in the condensing agent or in the condensing agent together with the solvent. The solvent referred to in step (a") may be the same as or different from the solvent referred to in step (b").

Process 4

According to yet another embodiment of the invention there is provided a process of preparing controlled release ceramic particles comprising:
- (a''') preparing a reverse micelle solution by mixing a surfactant with an apolar solvent;
- (b''') preparing an hydrophilic solution by dissolving a catalyst, a condensing agent and a (or several) soluble active material(s) in a polar solvent;
- (c''') preparing an emulsion by combining the reverse micelle solution and the hydrophilic solution;
- (d''') adding the gel precursor to the emulsion; and
- (e''') forming and aging controlled release ceramic particles, wherein each of said particles has the active material(s) substantially homogeneously dispersed throughout the particle and wherein the active material(s) is capable of being released from each of said particles, by condensing the precursor in the emulsion.

Usually the particles are substantially monodispersed.

Product of Process 1

According to another embodiment of the invention there is provided controlled release ceramic particles prepared by:
- (a) preparing a reverse micelle solution by mixing a surfactant with an apolar solvent;
- (b) preparing a precursor solution by dissolving a gel precursor, a catalyst, a condensing agent and a (or several) soluble active material(s) in a polar solvent;
- (c) preparing an emulsion by combining the reverse micelle solution and the precursor solution; and
- (d) forming and aging controlled release ceramic particles, wherein each of said particles has the active material substantially homogeneously dispersed throughout the particle and wherein the active material(s) is capable of being released from each of said particles, by condensing the precursor in the emulsion.

Usually the particles are substantially monodispersed.

Product of Process 2

According to yet another embodiment of the invention there is provided controlled release ceramic particles prepared by:
- (a') preparing a reverse micelle solution by mixing a surfactant with an apolar solvent and a (or several) hydrophilic first active material(s);
- (b') preparing a precursor solution by dissolving a gel precursor, a catalyst, a condensing agent and optionally a soluble second (or several) active material(s) in a polar solvent, which is immiscible with the apolar solvent used in (a');
- (c') preparing an emulsion by combining the reverse micelle solution and the precursor solution; and
- (d') forming and aging controlled release ceramic particles, wherein each of said particles has the active material(s) substantially homogeneously dispersed throughout the particle and wherein the active material(s) is capable of being released from each of said particles, by condensing the precursor in the emulsion.

Usually the particles are substantially monodispersed.

Product of Process 3

According to yet a further embodiment of the invention there is provided controlled release ceramic particles prepared by:
- (a") preparing a precursor solution by mixing a gel precursor, an (or several) active material(s) and optionally a solvent;
- (b") preparing a condensing solution by mixing a catalyst, a condensing agent and optionally a solvent, said condensing solution being substantially immiscible with said precursor solution;
- (c") combining the precursor solution and the condensing solution to form a mixture and preparing an emulsion by spontaneously emulsifying the mixture in the absence of a surfactant; and
- (d") forming and aging controlled release ceramic particles, wherein each of said particles has the active material(s) substantially homogeneously dispersed throughout the particle and wherein the active material(s) is capable of being released from each of said particles, by condensing the precursor in the emulsion.

Usually the particles are substantially monodispersed.

Product of Process 4

According to yet another embodiment of the invention there is provided controlled release ceramic particles prepared by:
- (a''') preparing a reverse micelle solution by mixing a surfactant with an apolar solvent;
- (b''') preparing an hydrophilic solution by dissolving a catalyst, a condensing agent and a (or several) soluble active material(s) in a polar solvent;
- (c''') preparing an emulsion by combining the reverse micelle solution and the hydrophilic solution;
- (d''') adding the gel precursor to the emulsion; and (e''') forming and aging controlled release ceramic particles, wherein each of said particles has the active material(s) substantially homogeneously dispersed throughout the particle and wherein the active material(s) is capable of being released from each of said particles, by condensing the precursor in the emulsion.

Usually the particles are substantially monodispersed.

The controlled release or substantially monodispersed controlled release ceramic particles prepared by the processes of the invention may be functionalised or derivatised.

Usually in the controlled release or substantially monodispersed controlled release ceramic particles prepared by the processes of the invention the active material(s) in said particles is substantially protected from degradation until release of the active material(s) from the particles.

The processes of the invention may include the steps of separating the ceramic particles and removing solution which typically comprises solvent and another material (such as surfactant) from the particles. The step of separating may be accomplished by known techniques such as filtering, washing, evaporating or decanting of the solvent and surfactant, for example.

The removal of the solvent (and surfactant) may be carried out by rinsing and/or washing of the ceramic particles with a suitable solvent or combination of solvents, followed by the taking off of remaining solvent from the particles. This may be accomplished by known techniques such as by absorption of the remaining solvent from the particles or by evaporating and/or drying of the ceramic particles for example.

Alternatively, the removal of the solvent (and surfactant) may be carried out after the separating by absorption of the solvent (and surfactant) from the particles or by evaporating and/or drying of the ceramic particles for example.

When solvent (and surfactant) has been removed from the ceramic particles they are commonly referred to as controlled release ceramic xerogel particles. Controlled release silica xerogel particles are particularly preferred.

Typically, NaCl or other suitable ionic salt (depending on the end use e.g. KI, KBr, KCl, NaBr, NaI, LiCl, LiBr, LiI, $CaCl_2$, $MgCl_2$, $NH_4NO_3$, $NaNO_3$, $KNO_3$, $LiNO_3$, etc.) is added to destabilise an emulsion after the ceramic particles have been formed therein. The inventors have found that without the addition of an ionic salt such as NaCl the wt % of residual surfactant on the resultant ceramic particles is much higher than when NaCl is used to break up the emulsion. The use of ($NaCl+CHCl_3$) for washing/emulsion breaking has led to <1.5 wt % residual surfactant on the resultant ceramic particles.

The purpose of removing surfactant is to avoid opsonisation (opsonisation: bonding of proteins and/or antibodies on the ceramic particles) since this determines whether or not the particles will be rejected from a subject. Preliminary testing of ceramic particles of the invention using a Protein Assay indicates: (a) particles with high surfactant (11.4 wt %): 40.5 µg of protein adsorbed; and (b) particles with low surfactant (2.4 wt %: 27 µg of protein adsorbed. Further it is preferred to wash by decantation to avoid aggregation during filtering (what is critical is the average size in solution).

One way of drying the particle, while preventing aggregation, is to freeze-dry the particles. The present inventors have found that this can be achieved by adding NaCl or other suitable ionic salt (e.g. NaBr, NaI, KI, KBr, KCl, LiI, LiCl, LiBr, etc.) to protect the particles during freeze drying and encapsulate the particles in a gangue of NaCl (FIG. 17).

Thus the processes of the invention may further comprise the steps of separating the formed and aged controlled release ceramic particles from the emulsion by adding an ionic salt to the emulsion whereby the particles are dispersed in a resulting solution, and freeze drying the solution, to form a solid in which unaggregated ceramic particles are isolated within a matrix of the ionic salt. This process may also include a step of washing the resulting solution. Typically the washing step is carried out to substantially reduce the amount of surfactant and other materials (typically the surfactant is reduced to less than 2 wt. %, typically 0.5-2 wt. %). By 'resulting solution' is meant a solution that forms when the emulsion is broken up by the addition of the ionic salt. Thus typically the resulting solution is an aqueous solution and the ionic salt is NaCl. In such a case the aqueous solution is typically washed with an organic solvent. Examples of suitable organic solvents include chloroform bromoform and iodoform,—other suitable organic solvents are known in the art.

Examples of drying processes are described in ACS Symposium 520, Polymeric delivery systems, properties and applications, I. C. Jacobs and N. S. Mason, Chapter 1, Polymer Delivery Systems Concepts, pp. 1-17, 1993, the contents of which are incorporated herein by cross reference.

Another embodiment of the invention provides a composition comprising controlled release ceramic particles according to the invention together with an acceptable carrier, diluent, excipient and/or adjuvant.

A further embodiment of the invention provides a method of treating a locus comprising applying controlled release ceramic particles of the invention or a composition according to the invention to the locus in an amount effective to treat the locus.

Another embodiment of the invention provides a method of treating an object comprising administering to the object controlled release ceramic particles of the invention or a composition according to the invention to the object in an amount effective to treat the object.

Yet a further embodiment of the invention provides a method of treating a subject comprising administering to the subject controlled release ceramic particles of the invention or a composition according to the invention to the subject in an amount effective to treat the subject.

The ceramic microparticles of the invention are prepared by a sol-gel based process in which partly hydrolysed oxides of suitable metals (including transition metals, silicon, etc.) are prepared in the presence of an active material by hydrolysis of the gel precursor followed by condensation (alternatively referred to as polycondensation). The gel precursor may be a metal oxide gel precursor including silicon oxide gel precursor, transition metal oxide precursor, etc. The identity of the gel precursor chosen that is, whether a silicon oxide gel precursor or a particular metal oxide gel precursor chosen for use in a process of the invention, will depend on the intended use of the ceramic particles and, in particular, the suitability of the final product resulting from the condensation of the gel precursor for the intended use of the ceramic particles. The gel precursor is typically a silica-based gel precursor, an alumina-based gel precursor, a titanium dioxide-based gel precursor, an iron oxide based gel precursor, a zirconium dioxide-based gel precursor or any combination thereof. A functionalised, derivatised or partially hydrolysed gel precursor may be used.

For silica there is a long list of potential silicon precursors which for convenience can be divided into 4 categories, the silicates (silicon acetate, silicic acid or salts thereof) the silsequioxanes and poly-silsequioxanes, the silicon alkoxides (from silicon methoxide ($C_1$) to silicon octadecyloxide ($C_{18}$)), and functionalised alkoxides for ORMOCER production (such as ethyltrimethoxysilane, aminopropyltriethoxysilane, vinyltrimethoxysilane, diethyldiethoxysilane, diphenyldiethoxysilane, etc). Further specific examples of silica-based gel precursors include tetramethoxysilane (TMOS), tetraethoxysilane (TEOS), tetrabutoxysilane (TBOS), tetrapropoxysilane (TPOS), polydiethoxysilane, methyltrimethoxysilane, methyltriethoxysilane, ethyltriethoxysilane, octylpolysilsesquioxane and hexylpolysilsesquioxane-.

Examples of alumina-based gel precursors include aluminium ethoxide, aluminium n- or iso-propoxide, aluminium n- or sec- or tert-butoxide. The alkoxide can also be modified using carboxylic acids (acetic, methacrylic, 2-ethylhexanoic, etc) or beta di-ketones such as acetylacetone, ethyl-acetylacetone, benzoylacetone, or other complexing agent. Upon hydrolysis, ORMOCER (Organically Modified Ceramics) particles are typically formed. As for silica they can be useful in preventing the interaction of the drug with the ceramic matrix.

Examples of titanium or zirconium gel precursors include the alkoxides (ethoxide, propoxide, butoxide), the metal salts (chloride, oxychloride, sulfate, nitrate) and the acid and beta diketone complexes.

The silica gel precursor or the metal oxide gel precursor may include from one to four alkoxide groups each having from 1 or more oxygen atoms, and from 1 to 18 carbon atoms, more typically from 1 to 5 carbon atoms. The alkoxide groups may be replaced by one or more suitable modifying groups or functionalised or derivatised by one or more suitable derivatizing groups (see K. Tsuru et al., J. Material Sci. Mater. Medicine, 1997, 8, the contents of which are incorporated herein by cross-reference).

Typically, the silica gel precursor is a silicon alkoxide or a silicon alkyl alkoxide.

Particular examples of suitable silicon alkoxide precursors include such as methoxide, ethoxide, iso-propoxide, butoxide and pentyl oxide. Particular examples of suitable silicon or metal alkyl (or phenyl) alkoxide precursors include methyl trimethoxysilane, di-methyldimethoxysilane, ethyltriethoxysilane, diethyldiethoxysilane, triethylmethoxysilane, phenyltriethoxysilane, diphenyldiethoxysilane, vinyltriethoxysilane, etc. Alternatively, the silica gel precursor may be a silicon carboxylate. For example, an acetate, tartrate, oxalate, lactate, propylate, formate, or citrate. Examples of other functional groups attached to silica gel precursors include esters, alkylamines and amides.

Typically, the metal oxide gel precursor is a metal alkoxide which may be derivatised or functionalised. Typically the transition metal oxide gel precursor is a transition metal alkoxide and the lanthanide metal oxide gel precursor is a lanthanide metal alkoxide. Examples of suitable metal oxide precursors include alkoxides such as methoxide, ethoxide, iso-propoxide, butyloxide and pentyl oxide. Alternatively, metal oxide gel precursor may be a metal carboxylate or a metal beta-diketonate, for example, an acetate, tartrate, oxalate, lactate, propylate, formate, citrate, or acetylacetonate. Examples of other functional groups attached to metal oxide precursors include esters, alkylamines and amides. More than one type of metal ion or lanthanide ion may be present (e.g. silicon titanium oxide, see example 23).

Sol-gel processing is based on the hydrolysis and condensation of appropriate precursors, which, in most cases, involves the reaction of an alkoxide (either modified or unmodified) with water (i.e. the hydrolysis step). Water is thus typically used as the condensing agent. Thus a typical reaction scheme may be represented as shown in FIG. 16.

Appropriate condensing agents other than water may be used where a non-aqueous sol-gel route is used via Process 3. Examples of several non-aqueous methods that are envisaged via process 3 are as follows:

Hydroxylation in non-aqueous systems.
Aprotic condensation reactions.
Ester elimination reaction by condensing alkoxides with carboxylate functional groups.
Ether elimination by condensing alkoxide with alkoxide, thus liberating dialkyl ether.
Oxolation not involving hydrolysis, via reaction of alkoxide with hydrogen halide or ketone (in the case of basic alkoxide such as Zn alkoxide).
Reactions of organic oxygen donors, such as dialkyl ether or dialkyl ketone, with metal halides.

The latter two reactions may be unsuitable for many applications since they involve the use of metal halides, which in turn generate chlorinated compounds which are highly toxic and could be difficult to remove by washing.

A suitable surfactant is a straight chain hydrocarbon having a hydrophilic head group such as, for example, a sorbitan, polyether, polyoxyethylene, sulfosuccinate, phosphate, carboxylate, sulfate, amino or acetylacetonate and a hydrophobic tail group. The tail group may be for example, straight or branched chain hydrocarbon which can have from about 8 to 24 carbon atoms, preferably from about 12 to 18 carbon atoms. It may contain aromatic moieties such as for example iso-octylphenyl.

(A) The first way to classify surfactants is according to their HLB's (Hydrophile Lypophile Balance, see page 48 of the M. F. Cox article in 'Detergents and Cleaners: A Handbook for Cleaners', Hanser/Gardner Publications, Inc., Ohio, USA. 1994, pp. 43-90, the contents of which (pp. 43-90) are incorporated by cross reference.

a) surfactants with HLB>10 are typically used for oil in water emulsions.
b) surfactants with HLB<10 are typically used for water in oil emulsions. A mixture of surfactants usually forms a more stable emulsion than either surfactant alone.

(B) Surfactants can also be classified according to their charge, i.e. cationic, anionic, or non ionic, although such a classification is not as relevant to the present invention. In general non-ionic surfactant are typically preferred, since they can be more easily removed by washing. The ionic type tends to complex the surfaces of oxide particles but can be often removed by changing the pH of the surface (i.e. washing with acid or base).

More relevant is the empirical classification by size. An extensive review of the literature on ceramic particle synthesis in emulsion suggests that:

1) Sorbitan esters (e.g. sorbitan monooleate, monopalmitate, monostearate), sold under the trade mark Span, may be used to provide particles >1 μm.
2) Alkylarylpolyether also called alkyl phenol ethoxylates, which are sold under the trade name Triton, may be used to provide particles smaller than 0.5 μm.
3) Alcohol ethoxylates are also used to synthesise nanoparticles in water-in-oil emulsions. They are sold under the trade names Brij (polyoxyethylene alkyl ether) and Tween (polyoxyethylene sorbitan alkylate). Typically such surfactants may be used to synthesise particles less than 1 μm.
4) AOT or aerosol OT or sodium bis(2-ethylhexyl)sulfosuccinate is an anionic surfactant used for synthesising particles from 5 nm to 1 μm.

There are also other surfactants which may be used such as block-copolymers.

The choice of the nature of the surfactant/solvent determines the particle size range.

The particle size increases with H (water/metal) and decreases with S (surfactant/metal):
Particle size increases with R (water/surfactant)
Droplet sizes increases with R
More water=larger droplets=larger micro-reactor The control of the particle size range is achieved by choice of the surfactant and adjustment of R (the particle size can be tailored in the range of 50-500 nm by changing R (water/surfactant) and/or surfactant/solvent. The catalyst may be an acidic or basic catalyst and is generally chosen so as to be compatible with the active material i.e. it is chosen so as not to deactivate the active material. Examples of acidic catalysts include mineral acids such as sulfuric acid, phosphoric acid, HCl and $HNO_3$. Organic acids such as acetic acid, tartaric acid, succinic acid and salicylic acid may be used. Examples of basic catalysts include NaOH, KOH, ammonium hydroxide, $Ca(OH)_2$, etc. Essentially the catalyst catalyses the reaction between the gel precursor and the condensing agent.

The pH and ionic strength of the solution in which the hydrolysis, micelle formation and aging occur can vary over a wide range depending on the nature of the active material. However, the rate of hydrolysis, the rate of aging or rate of polycondensation (also referred to herein as condensation) is affected by these parameters and can vary according to the metal oxide precursor. Generally, the pH used in the aging process can range from about 0-14, and is typically between about 1-11. When an acidic catalyst is used the pH range is typically 1-6.5, and even more typically 1-4.5. When a basic catalyst is used the pH range is typically 7-14, more typically 7-11. The pH at which the polycondensation (or condensation) is carried out is normally chosen so as to be at a value or within a certain pH range that does not substantially affect the activity of the active materials (which will depend on the nature of the active materials or the stability of the surfactant). One of ordinary skill in the art can determine optimal pHs and ionic strengths for particular gel precursors/active material combinations using the methods described herein, for example. Other ranges of pH in which the hydrolysis, micelle formation and aging may occur when an acidic catalyst is used are 1-7, 1-6, 1-5, 1-4, 1-3, 1-2, 2-7, 2-6, 2-5, 2-4, 2-3 ,3-7, 3-6, 3-5, 3-4, 4-7, 4-6, 4-5, 5-7, 5-6 or 6-7. Specific pH's in which the hydrolysis, micelle formation and aging may occur when an acidic catalyst is used include 1, 1.5, 2, 2.5, 3, 3.5, 4, 4.5, 5, 5.5, 6, 6.5 and 7. Other ranges of pH in which the hydrolysis, micelle formation and aging may occur when a basic catalyst is used are 7-14, 7-13, 7-12, 7-11, 7-10, 7-9, 7-8, 8-14, 8-13, 8-12, 8-11, 8-10 ,8-8, 9-14, 9-13, 9-12, 9-11, 9-10, 10-14, 11-13 or 11-12. Specific pH's in which the hydrolysis, micelle formation and aging may occur when a basic catalyst is used include 7.5, 8, 8.5, 9, 9.5, 10, 10.5, 11, 11.5, 12, 12.5, 13 and 13.5.

The maximum processing and aging temperatures are typically in the range 0-100° C. but more typically around room temperature, 20-30° C. The maximum temperatures of the processing and aging depends on the volatility of the solvent used. Typically the processing of the invention is carried out at a temperature in the range 1° C.-100° C., 0° C.-75-C., 0° C.-50°-C., 1° C.-50° C., 10° C.-100° C., 1° C.-75° C., more typically 0° C.-40° C., 1° C.-40° C., 5° C.-40° C., 10° C.-40° C., 15° C.-40° C., 20° C.-40° C., 25° C.-40° C., 30° C.-40° C., or 35° C.-40° C. Typically the aging is carried out at a temperature in the range 0° C.-100° C., more typically in the range 0° C.-75° C., 0° C.-50° C., 0° C.-40° C., 5° C.-40° C., 10° C.-40° C., 15° C.-40° C., 20° C.-40° C., 25° C.-40° C., 30° C.-40° C. or 35° C.-40° C.

The aging time is typically between 0-30 days but more typically from 30 min to 12 hr and even more typically of 1 hr. Typically the aging is carried out for a period in the range 30 minutes to 5 weeks, more typically 0.5 hours-4 weeks, 0.75 hours-4 weeks, 1 hour-4 weeks, 0.5 hours-3 weeks, 0.75 hours-3 weeks, 1 hour-3 weeks, 0.5 hours-2 weeks, 0.75 hours-2 weeks, 1 hour-2 weeks, 0.5 hours-1 week, 0.75 hours-1 week, 1 hour-1 week, 0.5 hours-5 days, 0.75 hours-5 days, 1 hour-5 days, 0.5 hours-3 days, 0.75 hours-3 days, 1 hour-3 days, 0.5 hours-2 days, 0.75 hours-2 days, 1 hour-2 days, 0.5 hours-1 day, 0.75 hours-1 day, 1 hour-1 day, 0.5 hours-20 hours, 0.75 hours-20 hours, 1 hour-20 hours, 1 hour-15 hours, 2 hours-15 hours, 3 hour-15 hours, 1 hour-10 hours, 2 hours-10 hours, 3 hours-10 hours, 1 hour-5 hours, 2 hours-5 hours, or 3 hours-5 hours.

The drying temperature can be from −196° C. (in liquid $N_2$ for freeze drying) to 300° C. for supercritical drying, but is more typically from 20° C. to 80° C. The maximum temperature is dictated by the thermal stability of the active ingredient(s) encapsulated in the particles. Typically drying is carried out at a temperature in the range 10° C.-50° C., more typically 12° C.-40° C., 15° C.-40° C., 17° C.-40 ° C., 19° C.-40° C., 20° C.-40° C., 25° C.-40° C., 30° C.-40° C. or 35° C.-40° C.

The drying time is typically between 30 minutes-30 days but more typically from 1 day to 1 week and even more typically 0.25, 0.5, 0.75, 1, 1.5, 2, 2.5, 3, 3.5, 4, 4.5, 5, 5.5 or 6 days.

The particle size can be tailored typically between 1 nm and 100 µm but more typically between 10 nm and 50 µm. The particle size of the controlled release ceramic particles may be in the ranges of 1 nm-100 µm, 1 nm-90 µm, 1 nm-80 µm, 1 nm-70 µm, 1 nm-60 µm, 1 nm-50 µm, 1 nm-40 µm, 1 nm-30 µm, 1 nm-20 µm, 1 nm-10 µm, 1 nm-7.51 µm, 1 nm-5 µm, 1 nm-2.5 µm, 1 nm-1.5 µm, 1 nm-1 µm, 1 nm-0.5 µm, 1 nm-0.1 µm, 1 nm-100 µm, 10 nm-50 µm, 10 nm-20 µm, 100 nm-100 µm, 100 nm-50 µm, 100 nm-10 µm, 100 nm-10 µm, 500 nm-100 µm, 500 nm-50 µm, 500 nm-10 µm, 500 nm-1 µm, 750 nm-100 µm, 750 nm-50 µm, 750 nm-10 µm, 750 nm-1 µm, 1-100 µm, 1-50 µm, 1-25 µm, 1-10 µm, 10-100 µm, 10-75 µm, 10-65 µm, 10-55 µm, 10-50 µm, 10-45 µm, 10-35 µm, 10-25 µm, 10-15 µm, 1-10 µm, 1-7.5 µm, 1-6.5 µm, 1-5.5 µm, 1-4.5 µm, 1-3.5 µm, 1-2.5 µm, 1-1.5 µm.

The elemental composition of the microparticles may affect their controlled release properties. Thus additives which result in elements such as C, Fe, Ti, N, Cl, Mg, P, Ca, K and/or Na, or other suitable elements being included in the ceramic particles may be added prior to any substantial polycondensation reaction occurring in the process of the invention to alter the composition of the particles as desired. Other examples of additives may be found in D. Avnir et al., Chemistry of Materials, 6, 1605-1614, 1994, the contents of which are incorporated herein by cross reference.

Other parameters which may be used to control the properties of the ceramic particles include gel precursor: water ratio, gel precursor: miscible solvent ratio, water: miscible solvent ratio, size of the ceramic particles, chemical composition of the ceramic particles, aging conditions and condensation rate.

The controlled release rate of the active material from the ceramic particles may be adjusted to the desired rate by appropriately adjusting the various parameters and additives mentioned throughout this specification.

The nature of the active materials in the compositions and methods of the invention will depend on the intended use. An effective amount of active materials is added to the appropriate mixture prior to polycondensation taking place to any significant extent.

More than one active material may be incorporated in the ceramic particles of the invention (e.g. 1, 2, 3, 4, 5, 6, 7, 8, 9, 10 or more active materials).

Active materials may be any biological active material such as organic, inorganic or organo metallic pharmaceutically active compounds, amino acids, polyamino acids, nucleic acids, polypeptides, proteins for example, hormones, enzymes, and globulins, and vitamins or mixtures thereof. Active materials which have been incorporated into liposomes and which have been described in G. Gregoriadis editor, 'Liposomes', Drug Carriers in Biology and Medicine, pp. 287-341, Academic Press, New York, 1979, the contents of which are incorporated herein by cross reference, may also be incorporated in the ceramic particles of the invention. Examples of the classes of pharmaceuticals from which a pharmaceutically active compound may be selected and incorporated in a ceramic particle of the invention via a process of the invention include antibiotics, antibacterials, analgesics, anaethetics, muscle relaxants, anti-inflammatories, antidepressants, anticoagulants, antipsychotics, antihypertensives, antiasthmatics, anticonvulsants, antivirals and antidiabetics. Examples of pharmaceutically active materials are disclosed in U.S. Pat. Nos. 4,952,402, 4,474,752 and 5,952,004 the contents of which are incorporated herein by cross reference. The active material may be a radiopharmaceutical (see for example U.S. Pat. Nos. 5,762,907, 5,550,160, and 5,496,533, the contents of which are incorporated herein by cross reference for a non comprehensive list examples of radiopharmaceuticals) including a radiolabelled protein (see for example U.S. Pat. No. 5,736,120 the contents of which are incorporated herein by cross reference for a non comprehensive list examples of radiolabelled proteins) and a radiolabelled carbohydrate or the active material may be a radiotracer. Typically the biologically active material is suitable for human use or veterinary use. Other classes of active materials include insecticides, fungicides, herbicides, miticides, nematicides, pesticides, antimicrobials, perfumes, fragrances, colorants or mixtures thereof.

The polar solvent used in the process of the invention may be water or a polar organic solvent. An organic solvent is typically used in some processes of the invention in addition to water used in the hydrolysis. Organic solvents that are miscible with water and are polar or solvents that can be partly dissolved in water can be used such as n-, sec- or tert-$C_1$-$C_6$ alkanols such as for example, methanol, ethanol, propanol, isopropanol, n-butanol, sec butanol or tert-butanol as well as ketones such as acetone, and methyl ethyl ketone, amines such as dipropylamine, esters such as methylacetate, water soluble ethers, polyhydric alcohols such as ethylene glycol or di- or tri-ethylene glycol. Examples of non-polar solvents that may be used in the process of the invention include alkanes (from hexane (C6) to dodecane (C12) and cycloalkanes such as cyclohexane), aromatic compounds (e.g. toluene, benzene) and commercial mixtures such as kerosene. In one process of the invention, for example, a metal gel precursor such as metal alkoxide is dissolved in a water miscible polar organic solvent such as, for example, ethanol. Water is added to the metal alkoxide solution (or water may be included in the organic solvent in the first instance). The active material is added to obtain a solution or dispersion. The active material may be added as a solution in the organic solvent or water or mixture of the organic solvent and water. A base (e.g. NaOH, KOH, $NH_3$, etc.) or an acid (HCl, $HNO_3$, acetic acid, formic acid, etc.) is added as catalyst (depending on the nature of the active material) so as to not adversely substantially affect the activity of the active material. The mixture is mixed at room temperature. The mixture is then added to a reverse micelle solution with stirring to form an emulsion and allowed to age (under stirring) so as to form substantially monodispersed ceramic particles. The substantially monodispersed particles are then typically separated from the combined mixture by standard techniques such as filtration and washing. Typically the surfactant is removed by washing with a solvent in which the active material is substantially insoluble or very slowly soluble. The ceramic particles are then typically dried and during the drying process any excess solvent is removed from the ceramic particles.

Other molecules may be attached to or coupled to or coated on the ceramic particles of the invention if desired. For example a targeting molecule such as an antibody or receptor molecule may be attached to or coupled to or coated on the ceramic particles of the invention. Examples of active targeting molecules are described in F. Carli, La Chimica & L'Industria, 404-498, 1993, L. Brannon-Peppas et al., Polymer News, 2, 316-318, and A. V. Kabanov and V. Y. Lalkhov, J. Controlled Release, 28, 15-35 (1994), the contents of all of which are incorporated herein by cross reference.

Applications of the invention include the delivery and controlled release of pharmaceuticals, hormones, proteins, etc. Controlled release of fertilisers, pesticides, herbicides, insecticides, biocides, perfumes, etc are also within the scope of the invention.

Where the controlled release ceramic particles are used in the form of a composition comprising controlled release ceramic particles, a carrier, diluent, excipient and/or adjuvant appropriate to the intended use is used. Thus where the active material is (a) a fertiliser—an agriculturally acceptable carrier, diluent, excipient and/or adjuvant is used; (b) a pesticide—a pesticidally acceptable carrier, diluent, excipient and/or adjuvant is used; (c) a herbicide—a herbicidally acceptable carrier, diluent, excipient and/or adjuvant is used; (d) an insecticide—an insecticidally acceptable carrier, diluent, excipient and/or adjuvant is used; (e) a biocide—a biocidally acceptable carrier, diluent, excipient and/or adjuvant is used; (f) a perfume—a carrier or diluent acceptable for a perfume is used; (g) a pharmaceutical—a carrier or diluent or adjuvant acceptable for pharmaceutical use; (h) a veterinary product—a carrier or diluent or adjuvant acceptable for veterinary use etc.

Advantageously in the method of the invention concerned with treating a subject the subject is a mammal or vertebrate. The mammal or vertebrate is typically selected from human, bovine, canine, caprine, ovine, leporine, equine, or feline vertebrate. Advantageously the vertebrate is a human, domestic fowl, bird, bovine, canine, ovine, leporine, equine, caprine, or feline vertebrate. Alternatively, the subject may be a fish, insect, or other suitable subject.

The composition may be a veterinarily acceptable composition or a pharmaceutically acceptable composition.

Typically, the mammal is a human and the composition is a pharmaceutically acceptable composition which comprises controlled release ceramic particles according to the invention and at least one pharmaceutically acceptable carrier, adjuvant and/or excipient. Where the animal is a mammal, the composition is generally a veterinarily acceptable composition which includes at least one veterinarily acceptable carrier, adjuvant and/or excipient together with controlled release ceramic particles of the invention. For parenteral administration, the controlled release ceramic particles of the invention of suitable size for the intended use may be prepared in sterile aqueous or oleaginous solution or suspension. Suitable non-toxic parenterally acceptable diluents or solvents include isotonic salt solution, water, ethanol, Ringer's solution, 1,3-butanediol, propylene glycol or polyethylene glycols in mixtures with water. Aqueous solutions or suspensions may further include one or more buffering agents. Examples of buffering agents include sodium citrate, sodium acetate, sodium borate or sodium tartrate.

Depending on the intended purpose, the dosage form of the composition will comprise from 0.01% to 99% by weight of the ceramic particles of the invention. Usually, dosage forms according to the invention will comprise from 0.01% to about 20%, more typically 0.05% to 15% and even more typically 0.1% to 5% by weight of the ceramic particles of the invention.

Compositions of the invention may be prepared by means known in the art for the preparation of compositions (such as in the art of preparing veterinary and pharmaceutical compositions) including blending, homogenising, suspending, emulsifying, dispersing and where appropriate, mixing of the ceramic particles together with the selected excipient(s), carrier(s), adjuvant(s) and/or diluent(s). However, the process of combining the particles of the invention with excipient(s), carrier(s), adjuvant(s) and/or diluent(s) should not be such as to destroy or substantially damage the ceramic particles.

In methods of administration the invention, the ceramic particles or compositions may be administered orally, topically, parenterally, e.g. by injection and by intra-arterial infusion, rectally or by inhalation spray or by way of a dermal patch.

A suitable treatment may comprise the application or administration of a single dose or multiple doses. If more than one type of ceramic particle is involved in the treatment each type of ceramic particle may be administered at the same time or at different times (including sequentially).

As indicated the administered dosage of the ceramic particles will vary and depends on several factors, such as the condition, age and size of the patient as well as the nature of the condition and the active materials and the effectiveness of the active materials. A typical dosage range may be from 0.0001 mg to 200 mg of active materials per kg in the case where an antimicrobial is the active material. Usually, the dose of an antimicrobial is in the range of from 0.001 mg to 10 mg per kg of body weight. For more specific details concerning various types of antimicrobials including sulfonamides, antibiotics, antifungals, antiprotozoans as well as dosage regimes see, for example, "Pharmacology and Drug Information for Nurses" Society of Hospital Pharmacists of Australia, W. B. Saunders, Harcourt Brace Jovanovich, Publishers, 3rd Edition, V. E. Richardson (edit.) Sydney, 1989, "Antibiotics: The Comprehensive Guide", I. K. M. Morton, J. Halliday, J. M. Hall and A. Fox, Consultants, Bloomsbury Publishing limited, London 1990, Remington's Pharmaceutical Sciences", A. R. Gennaro (edit.) Mack Publishing Company, Pennsylvania, 1990, Kirk-Othmer "Concise Encyclopedia of Chemical Technology" John Wiley & Sons, Inc., New York, N.Y., USA 1985, and "The Australian Guide To Prescription Drugs", M. Goyen, The Watermark Press, Sydney (1991) the contents of all of which are incorporated herein by cross reference.

Suspensions for oral administration may further comprise additives as required such as dispersing agents, suspending agents, and the like.

Solid forms for oral administration may contain pharmaceutically or veterinarily acceptable sweeteners, binders, disintegrating agents, flavourings, diluents, coating agents, preservatives, lubricants and/or time delay agents (chosen as to not substantially affect the controlled release mechanism). Liquid forms for oral administration may contain, in addition to the above agents, a liquid carrier.

Emulsions for oral administration may further comprise one or more emulsifying agents. For oral administration, the pharmaceutical or veterinary composition may be in the form of tablets, lozenges, pills, troches, capsules, elixirs, powders, including granules, suspensions, emulsions, syrups and tinctures. Slow-release, or delayed-release, forms may also be prepared, for example in the form of coated particles or multi-layer tablets or slow release capsules of ceramic particles.

Examples of dosage forms are as follows:
1. Tablet: Ceramic Particles Having Antimicrobial(s)—0.01 to 25 mg, generally 0.1 to 15 mg; Starch—5 to 25 mg; Lactose—80 to 280 mg; Gelatin—0 to 10 mg; and Magnesium stearate—0 to 10 mg.
2. Topical Cream: Ceramic Particles Having Antimicrobial(s) 0.1-15% (w/w), demineralized or distilled water—0.1-12% (w/w), surfactants 1-12% (w/w), thickening agents—0.1-3% (w/w), parabens 0.1-2% (w/w), vegetable oil 5-22% (w/w), mineral oil 0-12% (w/w), stearic acid 0-12% (w/w), and lanolin 0-12% (w/w).

The invention includes in particular compositions which are used for topical application which may be a cream, ointment, paste, solution, emulsion, lotion, milk, jelly, gel, stick, roll-on or smooth-on, wherein the ceramic particles comprises up to about 90%, more typically 10%, by weight of the composition, even more typically from about 0.1% to about 4% by weight, for example 3.5% by weight and the compositions include topically suitable carriers, diluents, excipients, adjuvants and other additives.

For topical administration, the pharmaceutical or veterinary composition may be in the form of a cream, ointment, gel, jelly, tincture, suspension or emulsion. The pharmaceutical composition may contain pharmaceutically acceptable binders, diluents, disintegrating agents, preservatives, lubricants, dispersing agents, suspending agents and/or emulsifying agents as exemplified above. The veterinary composition may contain veterinarily acceptable binders, diluents, disintegrating agents, preservatives, lubricants, dispersing agents, suspending agents and/or emulsifying agents as exemplified above. Other additives typically include bacteriocides, buffering agents, thickening agents and emollients.

Additionally, it will be understood that the topical compositions of the invention may include suitable colouring agents and/or perfumes well known in the art. Typical examples of suitable perfuming agents are provided in S. Arctander, "Perfume and Flavor Chemicals", Montclair, N.J., 1969.

It will be appreciated that the examples referred to above are illustrative only and other suitable carriers, diluents, excipients and adjuvants known to the art may be employed without departing from the spirit of the invention.

This invention involves a generic approach to the synthesis of sol-gel silica (and alumina, zirconia, or titania) matrices for controlling the release of bioactive materials over periods ranging from hours to months. Biological materials or other active materials are incorporated into the matrix during gelation at, or near, ambient temperature. Interactions between the matrix and the encapsulated species can be minimised by functionalisation of the surface using organically modified sol-gel precursors, such as methyltrimethoxysilane, vinyl trimethoxy silane, (3-glycidyloxypropyl) trimethoxysilane, etc:

The particles are produced in the form of substantially monodispersed controlled release ceramic particles, which are typically spherical, with an average size which can be varied typically in the range from 10 nm to 50 µm.

The diffusion rate of the encapsulated species may be varied by controlling the matrix structure (porosity, pore size and tortuosity) and particle size. Generally, the diffusion follows the law: $[C_t]/[C_0] = Dt^{-1/\alpha}$ where $C_0$ is the concentration of active material which has diffused out of the ceramic particles after time t=0 sec, $C_t$ is the concentration of active material which has diffused out of the ceramic particles after time t, D is the experimental diffusion coefficient of the active material and $\alpha$ is a parameter dependent on the properties of the particles affecting diffusion of the active material (e.g. pore size or diameter $\phi p$, tortuosity and size or effective diameter, $\Phi_m$, of the active material). Typically, when $\phi p/\phi_m > 10$ then $\alpha \approx 2$ (i.e. Fick's $1^{st}$ law), when $10 > \phi p/\phi_m > 2$ then $\alpha \approx d_s$ (where $d_s$ is the surface fractal dimension), and when $2 > \phi p/\phi_m$ the value of $\alpha$ has to be determined experimentally.

The release rate is a function of the diffusion of the encapsulated species in the matrix and matrix dissolution.

The external surface of the sol-gel oxide particles can be easily functionalised to promote bioadhesion, or to modify in-vivo biodistribution of the particles.

The invention provides a generic approach to the controlled delivery of a multitude of drugs and other active materials. The same matrix and particle sizes can be used with a wide range of different drugs and active materials.

The invention provides the possibility of producing different particle sizes for different applications with the same generic sol-gel chemistry.

The choice of particle size is determined by the specific application, rather than the drug or active material.

Easy functionalisation of the microspheres surface, to provide active targeting of the drug molecule or other active molecule.

Silica is bio-degradable and bio-compatible.

Relative mechanical stability of the matrix. No explosions or burst effects are observed as can occur with liposomes or reservoir systems.

Examples of Potential Applications
Controlled delivery of:
Pharmaceuticals for human health care application
subcutaneous delivery (microparticles)
intra-muscular delivery (microparticles)
intranasal and inhalation delivery system (microparticles)
vaginal applications (microparticles)
rectal applications (microparticles)
intravenous delivery (nanoparticles)
ocular delivery (nanoparticles)
passive organ targeting by size (liver, lungs)
transdermal patch (coating and microparticles) where:
    microparticles: 1 to 50 µm nanoparticles: 10 to 500 nm.
Drugs for veterinarian applications (see above);
Controlled release of:
Fertilisers;
Pesticides;
Herbicides;
Insecticides;
Biocides;
Perfumes

BRIEF DESCRIPTION OF THE DRAWINGS

FIG. 1-1: Influence of D (D=molar ratio of alcohol to silicon alkoxide) on the release from gels synthesised with W=8 (W=molar ratio of water to silicon alkoxide)

FIG. 1-2: Influence of W on the release from gels synthesised without methanol (D=0)

FIG. 2-1: Influence of the pH on the release for gels synthesised with W=4 and D=4. Acid region FIG. 2-2: Influence of the pH on the release for gels synthesised with W=4 and D=4. Basic region.

FIG. 3: Influence of MTMS (MTMS=methyltrimethoxysilane) substitution on release rate.

FIG. 4: Influence of the syneresis time on the release of Orange II (Orange II=(4-(2-hydroxy-naphthylazo) benzene sulfonic acid, sodium salt).

FIG. 5: Influence of the drying on the release from a gel synthesised with W=4 and D=0.

FIG. 7: Influence of the temperature of the release media on the release rate.

FIG. 8: Comparison of the release of gels containing Orange II and Methyl violet.

FIG. 9: Microspheres synthesised using a) heptane, b) octane c) dodecane and d) cyclohexane.

FIG. 10: Influence of the surfactant chain length on the size of the microspheres synthesised in dodecane. a) sorbitan monooleate and b) sorbitan monolaurate.

FIG. 11: SEM micrograph of nanospheres synthesised using an AOT/cyclohexane emulsion (AOT=Aerosol OT or sodium bis(2-ethyl hexyl)sulfosuccinate).

FIG. 12-1: Influence of the sol-gel chemistry on the release rate of microspheres.

FIG. 12-2: SEM micrographs of the surface of microspheres synthesised from sol-gel solutions at pH=2 and pH=9.

FIG. 13: Influence of the drying temperature of microspheres on their release kinetics.

FIG. 14: TEM micrograph showing the precipitation of platinum colloids in the aged TMOS derived gel containing cis-platin.

FIG. 15-1: Influence of the incorporation of MTMS on the release rate of cycloheximide.

FIG. 15-2: Influence of the incorporation of MTMS on the release rate of cis-platin.

FIG. 17-1: Freeze dried nanoparticles encapsulated in a gangue of sodium chloride.

FIG. 17-2 Redispersed nanoparticles in water-particles with an average particle size around 200 nm.

FIG. 17-3 Redispersed nanoparticles in water-graph showing a narrow size distribution.

FIG. 18-1 A TEM micrograph dried Cu-doped particles indicating that their diameter is ca. 50 nm.

FIG. 18-2 Photon correlation spectroscopy of a suspension of the particles of FIG. 18-1 confirming that the average particle size in solution was 51 nm.

FIG. 19 SEM of ceramic particles indicating that an increase in S leads to a corresponding decrease in the particle size.

FIG. 20 Graph showing particle size distributions of nanoparticles.

FIG. 21 SEM micrograph of particles prepared by process 3.

FIG. 22 SEM photograph of $TiO_2/SiO_2$ mixed oxide particles doped with Orange II prepared by process 1.

FIG. 23: Block diagram showing a preferred process 4 of the invention.

FIG. 24: Block diagram showing a preferred washing procedure in relation to process 4 of the invention.

BEST MODE AND OTHER MODES OF CARRYING OUT THE INVENTION

Figure 6:
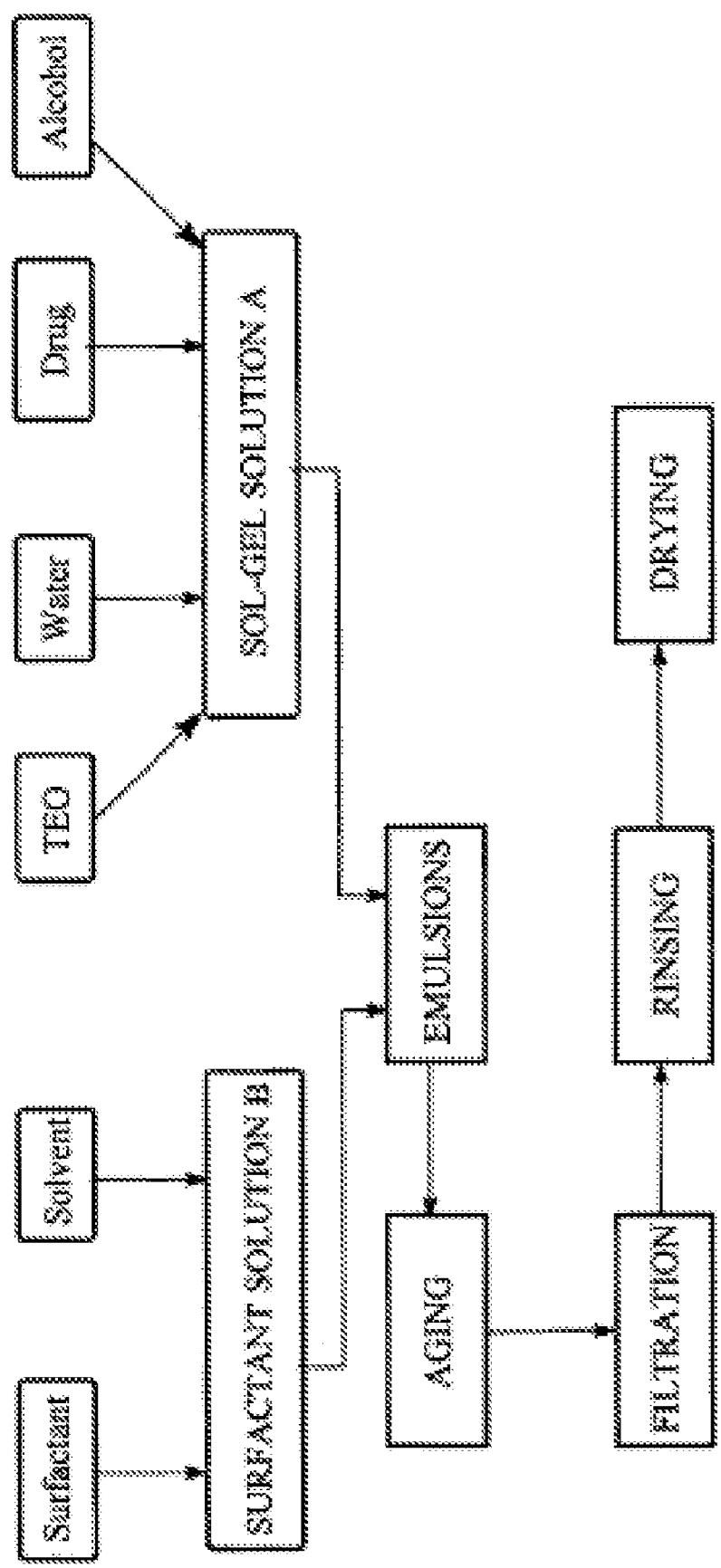
FIG. 6: Block diagram showing a preferred process 1 of the invention.
Figure 16:
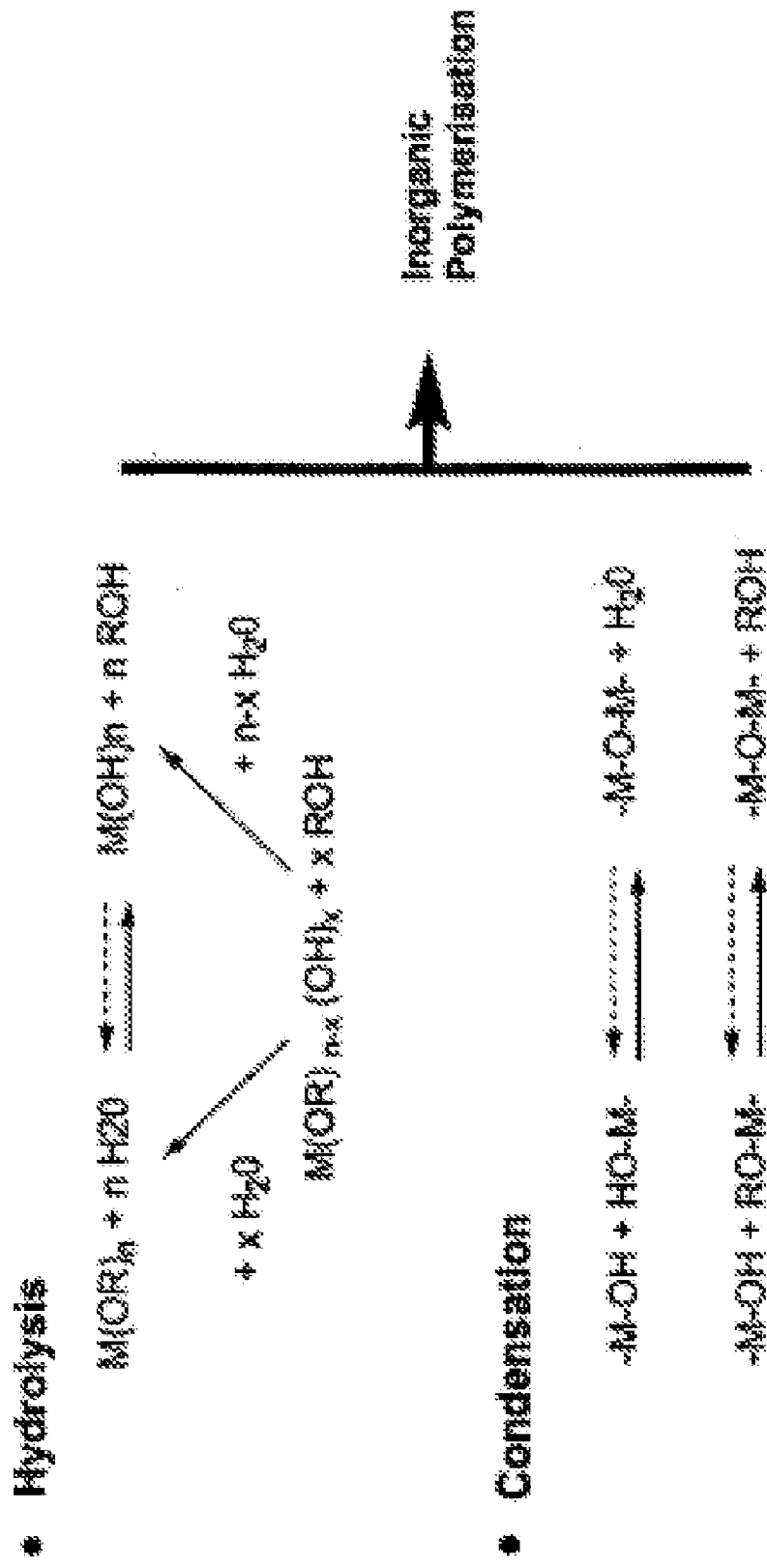
FIG. 16: Equations of hydrolysis and condensation.

FIG. 6 illustrates in block diagram form a preferred process of preparing substantially monodispersed controlled release ceramic particles, typically microspheres. The preferred process is described in detail below.

Gel Microsphere Preparation (Mainly Applicable to Process 1)

A sol-gel solution (solution A) is synthesised by adding a solution of silicon alkoxide (or organically modified silicon alkoxide) in alcohol to a solution of water in alcohol in which the bio-active molecules have been dissolved. The resulting mixture is set aside to start the condensation of the alkoxides into the corresponding metal oxide (i.e. silica).

A solution (solution B) is prepared by mixing a surfactant (eg. sorbitan mono-oleate, sorbitan mono-palmitate, AOT) with a non polar solvent. Solution B can be considered as a suspension of reverse micelles made by the surfactant.

Upon addition of A to B, the hydrophilic solution A migrates to the inside of the micelles forming an emulsion. The condensation reactions which have started upon addition of the water are accelerated upon such confinement. This leads to mass gelation of the liquid droplets and the production of substantially monodispersed controlled release porous silica microspheres containing the bioactive molecules trapped inside the pores. The particles are then filtered, washed to remove the surfactant and dried.

Controlled Release (Applicable to All Processes)

The internal matrix structure (especially pore size and tortuosity), particle size, overall active ingredient loading and/or matrix solubility determines the active ingredient delivery rates in controlled release systems. A significant limitation of polymeric controlled release matrices is that they can only exploit one, or at most two, of these features, and any changes in the active ingredient(s) necessitates a significant reformulation of the matrix system. In contrast, the present invention enables all of these features to be exploited using the same underlying chemistry:

The internal microstructure of the spheres can be precisely tailored (as in bulk gels) by varying such sol-gel processing parameters as the water-to-alkoxide ratio (W), pH, alcohol-to-alkoxide ratio, alkoxide concentration, aging (i.e. syneresis), drying time and temperature. Hence, the active ingredient(s) release rate is controlled by adapting the structure of the internal pore network (i.e. volume, diameter and tortuosity) to the physico-chemical properties of the active ingredient molecule.

The diameter of the ceramic particle is controlled by the size of the emulsion droplets, which is determined by the hydrophile-lipophile balance between the surfactant, aqueous phase and the non-polar solvent. Constant (zero-order) release rate can be obtained by fully entrapping the active ingredient(s) inside the silica matrix. The particles are produced in the form of substantially monodispersed spherical particles with a size which can be readily varied. The release rate of the active material is dependent on the size of the ceramic particle.

The overall active ingredient(s) loading within the microspheres is easily controlled during matrix synthesis.

The silica microspheres undergo slow in-vivo dissolution (erosion). Hence, the active ingredient release rate is a function of the active ingredient(s) diffusion rate inside the porous microspheres, the active ingredient loading and size of the microspheres.

Prevention of Surface Interaction (and Denaturation) Between the Matrix and the Active Ingredient (Applicable to All Processes).

The substitution of metal alkoxides by organically modified silicon alkoxides leads to the replacement of the hydroxyl groups at the surface of the pores by organic moieties (e.g. methyl vinyl, glycidyloxypropyl groups). This prevents interaction between the entrapped bio-molecules and the surface, and potential degradation of the active ingredient. This is illustrated by the encapsulation of cis-platin in silica gels. The cis-platin reacts with the surface of the silica matrix resulting in the precipitation of metallic platinum nanoparticles (see FIG. 14). The substitution of 50% of the tetra methoxy-silane (TMOS) by methyltri-methoxysilane (MTMS) prevents any such precipitation.

Process 1

One process of preparing substantially monodispersed controlled release ceramic particles typically comprises:
  a) preparing a reverse micelle solution by mixing a surfactant with an apolar solvent where typically the amount of surfactant is between 5-30 wt. % of the solvent;
  b) preparing a precursor solution by dissolving a gel precursor, a catalyst, a condensing agent and a (or several) soluble active material(s) in a polar solvent comprising water and alcohol where typically the water to precursor molar ratio is between 2 and 8, the alcohol to precursor molar ratio is between 0 and 16, the pH is between 1 and 11, and the proportion of active material is between 0.1-10 mg/g of final metal oxide;
  c) preparing an emulsion by combining the reverse micelle solution and the precursor solution where typically the proportion of reverse micelle solution to precursor solution is adjusted so that the surfactant to oxide gel precursor molar ratio is between 0.1-10, more typically a ratio of 0.5-2; and
  d) forming and aging substantially monodispersed controlled release ceramic particles, wherein each of said particles has the active material(s) substantially homogeneously dispersed throughout the particle, by condensing the precursor in the emulsion.

Typically the gel precursor is selected from the group consisting of a silica precursor, an alumina precursor and a titania precursor and more typically the gel precursor is a silica gel precursor.

Typically step (d) comprises:
  (d) forming and aging substantially monodispersed controlled release ceramic particles, wherein each of said particles has the active material substantially homogeneously dispersed throughout the particle, the active material is capable of being released from said particle and the active material in said particles is incorporated so as to be substantially protected from degradation until release of the active material from the particles, by condensing the precursor in the emulsion.

The process may further comprise:
  (e) separating said formed and aged controlled release ceramic particles from said emulsion.

The process may further comprise:
(e) removing surfactant from said formed and aged controlled release ceramic particles.

Process 2

An alternative process of preparing substantially monodispersed controlled release ceramic particles typically comprises:
(a') preparing a reverse micelle solution by mixing a surfactant with an apolar solvent and a hydrophilic first (or several) active material(s) where typically the amount of surfactant is between 5-30 wt % of the solvent and the proportion of active material(s) is between 0.1-1 wt % of final metal oxide;
(b') preparing a precursor solution by dissolving a gel precursor, a catalyst, a condensing agent and optionally a (or several) soluble second active material(s) in a polar solvent (which is immiscible with the apolar solvent in (a')) comprising water and alcohol where typically the water to precursor molar ratio is between 2 and 8, the alcohol to precursor molar ratio is between 0 and 16, the pH is between 1 and 11, and the proportion of second active material is between 0.1-10 mg/g of final metal oxide;
(c') preparing an emulsion by combining the reverse micelle solution and the precursor solution; the proportion of reverse micelle solution to precursor solution is adjusted so that the surfactant to oxide gel precursor molar ratio is between 0.1-10 where typically this molar ratio is of 0.5-2; and
(d') forming and aging substantially monodispersed controlled release ceramic particles, wherein each of said particles has the active material(s) substantially homogeneously dispersed throughout the particle, by condensing the precursor in the emulsion.

Typically the gel precursor is a silica gel precursor.
Typically step (d') comprises:
(d') forming and aging controlled release ceramic particles, wherein each of said particles has the active material substantially homogeneously dispersed throughout the particle, the active material is capable of being released from said particle and the active material in each of said particles is incorporated so as to be substantially protected from degradation until release of the active material from the particle, by condensing the precursor in the emulsion.

The process may further comprise:
(e') separating said formed and aged controlled release ceramic particles from said emulsion.

The process may further comprise:
(e') removing surfactant from said formed and aged controlled release ceramic particles.

Process 3

Another process of preparing substantially monodispersed controlled release ceramic particles comprises:
(a") preparing a precursor solution by dissolving a gel precursor (TEOS), an (or several) active material(s) (active material(s) is (are) soluble in TEOS by itself or in TEOS/solvent mixture) and optionally a small quantity of solvent (ethanol);
(b") preparing a condensing solution comprising a catalyst (acid or base or both sequentially), a condensing agent (H2O) and optionally a small quantity of solvent (ethanol), said condensing solution being substantially immiscible with said precursor solution;
(c") combining the precursor solution and the condensing solution to form a mixture and preparing an emulsion by spontaneously emulsifying the mixture in the absence of a surfactant;
(d") forming and aging substantially monodispersed controlled release ceramic particles, wherein each of said particles has the active material(s) substantially homogeneously dispersed throughout the particle and wherein the active material(s) is capable of being released from said particle, by condensing the precursor in the emulsion.

Typically the gel precursor is a silica gel precursor.
Typically step (d") comprises:
(d") forming and aging controlled release ceramic particles, wherein each of said particles has the active material substantially homogeneously dispersed throughout the particle, the active material is capable of being released from each of said particles and the active material in each of said particles is incorporated so as to be substantially protected from degradation until release of the active material from the particle, by condensing the precursor in the emulsion.

The process may further comprise:
(e") removing surfactant from said formed and aged controlled release ceramic particles.

Process 4

Another process of preparing substantially monodispersed controlled release ceramic particles comprises:
a''') preparing a reverse micelle solution by mixing a surfactant with an apolar solvent where typically the amount of surfactant is between 1-30 wt. % of the solvent;
b''') preparing an hydrophilic solution by dissolving a catalyst, a condensing agent and a (or several) soluble active material(s) in a polar solvent comprising water.
c''') preparing an emulsion by combining the reverse micelle solution and the hydrophilic solution.
d''') adding a gel precursor to this emulsion where typically the proportion of reverse micelle solution to precursor is adjusted so that the surfactant to oxide gel precursor molar ratio is between 0.1-10, more typically a ratio of 5-2; and
e''') forming and aging substantially monodispersed controlled release ceramic particles, wherein each of said particles has the active material(s) substantially homogeneously dispersed throughout the particle, by condensing the precursor in the emulsion.

The step (d''') comprises:
(d''') adding a silica gel precursor to the emulsion.
Typically step (e''') comprises:
(e''') forming and aging controlled release ceramic particles, wherein each of said particles has the active material substantially homogeneously dispersed throughout the particle, the active material is capable of being released from each of said particles and the active material in each of said particles is incorporated within said particle so as to be substantially protected from degradation until release of the active material from the particle, by condensing the precursor in the emulsion.

The process may further comprise:
(e''') separating said formed and aged controlled release ceramic particles from said emulsion.

The process may further comprise:
(e''') removing surfactant from said formed and aged controlled release ceramic particles.

FIG. 23 illustrates in block diagram form a preferred process of preparing substantially monodispersed controlled release ceramic particles, typically nanospheres. The preferred process is described in detail below.

Gel Nanosphere Preparation (Applicable Mainly to Process 4)

A reverse micelle solution is prepared by mixing a surfactant (typically a surfactant which does not substantially interact with the active being used—e.g. $CU(NH_3)_4+$ ionic surfactant leads to loss of $Cu(NH_3)_4$ in the washing step whereas with $Cu(NH_3)_4+$ non ionic surfactant loadings of 1-35 wt. % Cu have been achieved) with an apolar solvent where typically the amount of surfactant is between 5-30 wt. % of the solvent (solution A). A hydrophilic solution is prepared by dissolving a catalyst, a condensing agent and a (or several) soluble active materials (such as a pharmaceutical or radiopharmaceutical tracer e.g. Cu, Pt, . . . ) in a polar solvent comprising water (solution B). An emulsion is prepared by combining the reverse micelle solution (Solution A) and the hydrophilic solution (Solution B). A gel precursor is added to this emulsion where typically the proportion of reverse micelle solution to precursor is adjusted so that the surfactant to oxide gel precursor molar ratio is between 0.1-10, more typically a ratio of 0.5-2 whereby the precursor condenses in the emulsion thereby forming and aging controlled release ceramic nanoparticles, wherein each of said particles has the active material substantially homogeneously dispersed throughout the particle, the active material is capable of being released from each of said particles and the active material in each of said particles is incorporated within said particle so as to be substantially protected from degradation until release of the active material from the particle.

FIG. 24 depicts a block diagram showing a preferred washing procedure. In essence an ionic salt such as NaCl solution (e.g. 0.1-10M, typically 0.5-5M, more typically 1M) is added in a sufficient quantity to destabilise the emulsion. This destabilised emulsion is then washed a number of times with an organic solvent (eg $NaCl+CHCl_3$ and/or bromoform and/or iodoform) which is decanted off. The washed aqueous suspension is then freeze dried to form a solid in which unaggregated ceramic nanospheres are isolated within a matrix of the NaCl.

It has been found by the inventors that the presence of NaCl protects the ceramic particles during the freeze drying process. As indicated above as a result of this process the unaggregated freeze dried particles are isolated in a protective NaCl matrix (other ionic salts may be used particularly for non-biological uses but NaCl is particularly suited for biological applications, especially in vivo biological applications related to mammals including humans). The doped, freeze dried, ceramic nanoparticles may be irradiated, then redispersed in an appropriate amount of water to provide an isotonic solution and, if required, the solution may be injected for in vivo treatment, diagnosis or studies.

EXAMPLES

A) Influence of the Sol-Gel Processing Parameters on the Release of Orange II

Example 1

Influence of the Methanol/TMOS and $H_2O$/TMOS Molar Ratios on the Release Rate of Orange II A solution of dye was produced by dissolving 0.25 g of 4-(2-hydroxy-1-napthylazo) benzene sulfonic acid, sodium salt (i.e. Orange II, Aldrich) in 25 ml of a 0.1M nitric acid solution and diluting to 250 ml with demineralised water. The final pH of the dye solution was 2.

Gels were synthesised by combining tetramethylorthosilicate (TMOS), methanol (MeOH), and the dye solution. The influence of $H_2O$/TMOS ratio (W) and MeOH/TMOS ratio (D) on the dye release rate was studied by using the compositions listed in Table 1.

TABLE 1

Compositions of gels synthesised with different W and D.

|  | D = 0 | D = 4 | D = 8 |
|---|---|---|---|
| W = 2 | TMOS (8.10 ml, 54.4 mmol) $H_2O^1$ (1.96 ml, 109 mmol) | TMOS (5.00 ml, 33.6 mmol) $H_2O$ (1.21 ml, 67.2 mmol) MeOH (5.44 ml, 134 mmol) | TMOS (3.00 ml, 20.2 mmol) $H_2O$ (0.73 ml, 40.3 mmol) MeOH (6.54 ml, 161 mmol) |
| W = 4 | TMOS (8.10 ml, 54.4 mmol) $H_2O$ (3.92 ml, 218 mmol) | TMOS (4.00 ml, 26.9 mmol) $H_2O$ (1.94 ml, 108 mmol) MeOH (4.36, 108 mmol) | TMOS (3.00 ml, 20.2 mmol) $H_2O$ (1.45 ml, 80.6 mmol) MeOH (6.54 ml, 161 mmol) |
| W = 8 | TMOS (7.00 ml, 47.0 mmol) $H_2O$ (6.78 ml, 376 mmol) | TMOS (4.00 ml, 26.9 mmol) $H_2O$ (3.88 ml, 215 mmol) MeOH (4.36 ml, 108 mmol) | TMOS (3.00 ml, 20.2 mmol) $H_2O$ (2.91 ml, 161 mmol) MeOH (6.54 ml, 161 mmol) |

[1]Water is added in the form of the Orange II dye solution.

The resulting mixtures were stirred for 1 h. 4 ml aliquots of the solutions were transferred to 5 ml screw capped polypropylene vials and placed at 60° C. in an oven to gel. Once gelation occurred, the samples were aged at 60° C. for two more days. For each composition, one gel rod was set apart to study the release in the wet state and the remaining gel rods were dried at 60° C. for 3 days. In the following, the gel rods remaining in the wet state will be labelled as "wet gels" while those dried at 60° C. will be referred to as "dry gels".

The release of the dye molecule from the gels was performed in 3 ml of demineralised water and the evolution of the absorbance with time was monitored at a fixed wavelength $\lambda_{max}$=485 nm using a UV-visible spectrophotometer (Lambda 40, Perkin Elmer, USA). The wavelength of 485 nm corresponds to the absorbance maximum of Orange II in the visible spectrum.

The plots of fraction of dye released versus time (FIG. 1) were obtained by dividing the actual quantity of dye released by the total mass of dye encapsulated in the gel. For the dry gel, this quantity is calculated by dividing the total quantity of dye in the gel rod by the mass of the gel and multiplying it by the mass of the gel sample used in the release experiments. For the wet gel, the fraction released was obtained experimentally from the final absorbance.

The release rate of the dye was found to increase with increasing W and decreasing D. Note that constant release rates were obtained for compositions 1/8/4 and 1/4/0.

Example 2

Influence of the pH on the Release Rate of Orange II

To study the influence of pH, gels were prepared by adjusting the pH of the dye solutions to 1, 2, 4, 7, 9 or 11.

The different dye solutions were produced by dissolving 0.10 g of Orange II dye in 100 ml of nitric acid (0.1 M) or aqueous ammonia (0.1M) and further adjusting, by titration, the pH to the desired value.

The gels were synthesised by mixing 5.51 ml of TMOS (37 mmol), 2.67 ml of dye solution at the appropriate pH (148 mmol of water) and 6 ml of methanol (148 mmol). The samples were then aged and dried according to the procedure described in Example 1. The corresponding release curves are presented in FIG. 2.

For gel synthesised using acid as a catalyst (FIG. 2-1), the release rate was found to increase with increasing pH. In contrast, for the gel synthesised using base as a catalyst, the release was found to decrease with increasing pH. The maximum release rate was observed at pH=7.

Example 3

Influence of MTMS/TMOS Ratio

Gels were synthesised according to the procedure described in Example 1 but substituting 0-50% of TMOS with equimolar quantities of methyltrimethoxysilane (MTMS, Fluka). W and D were both fixed to 4, corresponding to 2.67 ml of dye solution at pH=2 ($H_2O$=148 mmol) and 6.00 ml of methanol (148 mmol).

TABLE 2

Compositions of gels synthesised with various MTMS/TMOS molar ratios.

| MTMS (mol %) | |
|---|---|
| 0% | TMOS (5.51 ml, 37.0 mmol) |
| 10% | TMOS (4.96 ml, 33.3 mmol), MTMS (0.53 ml, 3.70 mmol) |
| 20% | TMOS (4.41 ml, 29.6 mmol), MTMS (1.06 ml, 7.41 mmol) |
| 30% | TMOS (3.86 ml, 25.9 mmol), MTMS (1.59 ml, 11.1 mmol) |
| 40% | TMOS (3.31 ml, 22.2 mmol), MTMS (2.11 ml, 14.8 mmol) |
| 50% | TMOS (2.78 ml, 18.5 mmol), MTMS (2.64 ml, 18.5 mmol) |

The corresponding release kinetics are shown in FIG. 3. The release rate was found to decrease with increasing MTMS content.

Example 4

Influence of the Syneresis Time on the Release Rate of Orange II

A series of gels was synthesised by varying the syneresis time from 0 to 30 days.

A stock solution containing 30.3 ml of TMOS (204 mmol), 14.7 ml of Orange II dye solution at pH 2 (815 mmol) and 33.0 ml of methanol (815 mmol) was stirred for 1 h. 4 ml aliquots of this solution were transferred to 5 ml screw capped poly-propylene vials and placed in an oven at 60° C. to gel. The resulting gels were further aged at 60° C. for 0, 2, 3, 7, 15 and 30 days. The vials were subsequently uncapped and the aged gels were dried in the oven at 60° C. for 3 days. The release experiments were conducted following the procedure described in Example 1. The corresponding release curves are presented in FIG. 4.

The release rate was found to increase with syneresis time.

Example 5

Influence of the Drying Temperature and Time on the Release Rate of Orange II

A stock solution containing 78.6 g TMOS (516 mmol) and 37.3 g of Orange II dye solution at pH 2 (2.07 mol of $H_2O$) was stirred for 1 h. 4 ml aliquots of this solution were transferred to 5 ml screw capped poly-propylene vials and placed at 60° C. in an oven to gel. The resulting gels were further aged at 60° C. for two days. The aged gels were then dried for 1, 3 or 7 days at ambient (i.e. 22-23° C.), 60° or 104° C. The release experiments were conducted following the procedure described in Example 1. The corresponding release kinetics are presented in FIG. 5.

The release rate was found to decrease with increasing time and temperature.

B) Influence of Other Parameters on the Release Rate of Orange II

Example 6

Influence of the Environment on the Release Rate of Orange II

Gels were synthesised according to the procedure described in Example 1. The water/alkoxide and the methanol/alkoxide molar ratio were both fixed to 4, corresponding to 2.67 ml of dye solution at pH=2 (148 mmol of $H_2O$) and 6.00 ml of methanol (148 mmol) for 5.51 ml of TMOS (37 mmol). The gels were then dried at room temperature for 1 day.

To study the influence of the temperature on the release rate, a known quantity of gel was immersed in 3 ml of demineralised water and the absorbance was monitored at a fixed wavelength of 485 nm. One sample was kept at ambient temperature (i.e. 22° C.) and two others were maintained at 37° C. and 60° C. in thermostated water baths. The corresponding release kinetics are presented in FIG. 7. The release rate was found to increase with increasing temperature.

Example 7

Comparison Between the Release Kinetics of Orange II and Methyl Violet

A methyl violet solution was prepared by dissolving 0.112 g of the dye powder (Aldrich) in 5 ml of methanol and diluting the resulting solution with 100 ml of 0.1M nitric acid. The final pH of the solution was adjusted to 2. A solution of the Orange II dye was prepared as described in Example 1.

Two sets of gels were prepared by combining tetramethylorthosilicat-e (TMOS), methanol (MeOH), and each of the dye solutions. W and D were both fixed to 4, corresponding to 2.67 ml of dye solution (148 mmol of $H_2O$), 6 ml of methanol (148 mmol) and 5.51 ml of TMOS (37 mmol). 4 ml aliquots of these solutions were transferred to 5 ml screw capped poly-propylene vials and placed in an oven at 60° C. to gel. The resulting gels were further aged at 60° C., for 15 or 30 days, before being dried for 2 days at 60° C.

The release rates of the Orange II samples were monitored at a fixed wavelength of 485 nm while the release rates of the methyl-violet samples were monitored at 584 nm (corresponding to the absorption peak of methyl-violet in the visible spectrum). The corresponding release kinetics are presented in FIG. 8.

The release rate was found to be significantly smaller for the larger dye molecule (i.e. methyl violet)

C) Parameters Controlling the Size of Microspheres

Example 8

Synthesis of Microspheres with Different Size by Changing the Emulsion Solvent

A sol-gel solution (solution A) was prepared by combining 5.21 ml of TMOS (35 mmol), 2.52 ml of Orange II dye solution at pH=2 (as per Example 1) (140 mmol of $H_2O$) and 6.19 ml of methanol (153 mmol). The resulting solution was stirred for 30 min. at 300 rpm and left to age for 1 day at room temperature.

15.08 g of sorbitan monooleate was dissolved in 170 ml of kerosene and homogenised using a high speed blender (1200 rpm for 45 s) to form a clear solution (solution B). Solution A was then added to solution B and the resulting emulsion was stirred at 500 rpm for 1 h. The resulting suspension of microspheres was then filtered and rinsed three times with cyclohexane to remove the surfactant. The resulting microspheres were then dried for 1 day at room temperature before further drying at 60° C. for 3 days. The procedure was repeated using hexane, heptane, octane, decane, dodecane and cyclohexane as the emulsion solvent. Selected scanning electron micrographs of the dried microspheres obtained using these solvents are presented in FIG. 9.

The average size of the microspheres was found to decrease with decreasing polarity of the solvent (i.e. heptane>octane>dodecane>-; cyclohexane).

Example 9

Influence of the Surfactant Chain Length on the Size of the Microspheres

To study the influence of the surfactant chain length on the size of the microspheres, samples were prepared according to the procedure described in example 8 but with sorbitan monooleate replaced by sorbitan monolaurate (12.1 g). As in example 8, a series of experiments was performed using various solvent, such as hexane, octane, decane and dodecane. An example of the influence of the surfactant chain length on the microspheres size is presented in FIG. 10. In this instance, increasing the hydrophobic chain length decreases the size of the microsphere. However, it should be noted that whether this effect is observed or not will be dependent on the particular surfactant/non-polar solvent combination used. Whether or not the effect is present for a particular surfactant/non-polar solvent combination can be readily checked by routine experiment.

Example 10

Synthesis of Nano-Spheres Using AOT as the Surfactant 4.46 g of AOT (10 mmol) was dissolved in 100 ml of cyclohexane and mixed with 1.26 g of Orange II dye solution at pH=2 (70 mmol of $H_2O$) to form a stable micro-emulsion. 2.66 g of TMOS (17 mmol) was then added to the microemulsion and the resulting mixture was stirred for 1 day.

The resulting precipitate was filtered and washed with cyclohexane. The washed solid was then dried at room temperature. The corresponding scanning electron micrograph is shown in FIG. 11. In this case, nanospheres are produced (i.e. size.apprxeq. 100 nm) instead of microspheres.

Example 11

Synthesis of Microspheres with Different Sol-Gel Chemistry

The microspheres were prepared according to the procedure given in example 8 but using three different sol-gel chemistries. In each cases, the sol-gel solutions (solution A in example 8) were prepared by mixing 5.33 g of TMOS (35 mmol) with 4.9 g of methanol (153 mmol) and adding 2.52 g of Orange II dye solution (140 mmol of $H_2O$). In the first sample, the dye solution was prepared at pH=2, while in the second, the dye solution was prepared at pH=11. In the third case TMOS was partially substituted by MTMS (i.e. 20 mol %). The corresponding release curves are presented in FIG. 12-1. An example of the influence of pH on the internal microstructure of the microspheres is given in FIG. 12-2. The microspheres produced at pH=2 present a smooth surface which correspond to a microporous internal structure while the microspheres produced at pH=11 possess a rough surface denoting a mesoporous internal structure. FIG. 12-1 and FIG. 13 show that the internal structure of the sphere strongly influences their release rate.

Example 12

Influence of the Drying Temperature on the Release Rate of Microspheres

Microspheres containing orange II dye were synthesised according to the procedure described in example 8. The resulting microspheres were then dried at different temperatures from ambient to 100° C. for 2 days. The corresponding release kinetics are presented in FIG. 13. As for example 5, the release rate decreases with increasing drying temperature.

Example 13

Prevention of Drug Degradation by Surface Functionalisation

A solution of cis-platin (Cis $Pt(NH_3)_2Cl_2$) was prepared by dissolving 50.0 mg of cis-platin in 50 ml of 0.01M HCl solution and sonicating the solution for 15 minutes using a Branson 3200 sonication bath.

A solution containing 20 ml of TMOS (134 mmol), 9.69 ml of cis-platin solution (538 mmol of water) and 21.8 ml of methanol (538 mmol) was stirred for 30 minutes. 4 ml aliquots of the solution were transferred to 5 ml screw capped poly-propylene vials and placed in an oven at 60° C. to gel. Once gelation occurred the samples were aged at 60° C. for 15 days. The cap was then removed and the samples were allowed to dry for 3 days at 60° C.

An identical procedure was used to prepare gels from a solution containing 3 ml of TMOS, 2.88 ml of MTMS and 2.91 ml of cis-platin solution.

After 3 days of aging at 60° C. the gels prepared from TMOS started to darken, ultimately yielding a black gel after 15 days aging. In the contrast the gels prepared from MTMS/TMOS mixtures remained perfectly transparent even after 15 days aging at 60° C. The two dry gels were subsequently examined by transmission electron microscopy using a JEOL 201 OF field emission gun microscope. The black gel was found to contain small platinum colloids (.apprxeq. 50-80 nm in size) dispersed throughout the silica matrix (see FIG. 14). No such colloids were found to be present in the MTMS modified gels suggesting that the surface methyl groups present in the MTMS functionalised gels minimizes interaction of the cis-platin with the matrix and its associated precipitation.

Example 14

Influence of the Presence of MTMS on the Release of Cis-Platin and Cycloheximide A solution of cycloheximide was prepared by dissolving 25.0 mg of cycloheximide in 25 ml of 0.01M HCl solution (pH=2). A solution of cis-platin (1 g/l) was prepared by dissolving 50.0 mg of cis-platin in 50 ml of 0.1M HCl solution and sonicating the resulting solution for 15 minutes.

The first series of samples was prepared by mixing 5.51 ml of TMOS (37 mmol), 2.67 ml of either drug solutions (148 mmol of $H_2O$) and 6 ml of methanol (148 mmol). 4 ml aliquots of the solutions were transferred to 5 ml screw capped poly-propylene vials and placed in an oven at 60° C. to gel. Once gelation occurred the samples were aged at 60° C. for 7 days. The cap was then removed and the samples were allowed to dry for 3 days at 60° C.

A second series of samples was prepared by combining 3 ml of TMOS (20 mmol), 2.88 ml of MTMS (20 mmol) and 2.91 ml of the respective drug solution (161 mmol of $H_2O$). These samples were processed as described above.

The release of cycloheximide from a known quantity of gel was investigated in 3 ml of demineralised water and the absorbance was monitored at a fixed wavelength, $\lambda_{max}$=201 nm. The release of cis-platin from a known quantity of gel was investigated in 3 ml of 0.9% NaCl and the absorbance was monitored at a fixed wavelength, $\lambda_{max}$=300 nm. The corresponding release kinetics are presented in FIGS. 15-1 and 15-2.

As expected (cf. example 7), the release rate was found to be greater for the smaller drug molecule (i.e. cis-platin). As for Orange II (cf. example 3), substitution of TMOS by MTMS led to a decrease in the release rate of both drugs.

Example 15

Synthesis of Cu Doped Silica Nanoparticles Using Process 4

A copper tetraamine solution (i.e. solution 1) was prepared by dissolving $Cu(NO_3)_2.3H_2O$ (4.38 g, 18 mmol) in 10 ml of concentrated ammonia solution and diluting the resulting solution to 100 ml with distilled water. Triton X-114 (10.72 g, 20 mmol) was dissolved in 100 ml of toluene, and a microemulsion was subsequently produced by adding 5.76 ml of solution 1 (32 mmol equivalent of $H_2O$) and homogenising the resulting mixture by shear-mixing at 8000 rpm for 1 min. The emulsion was then stirred at 300 rpm and 0.3 ml of TMOS (2 mmol) was added. After stirring for 90 minutes, 50 ml of a 1M solution of NaCl was added to the emulsion and the resulting suspension was transferred to a decantation funnel. After 12 hours the emulsion had separated into two phases. The aqueous (bottom) phase was extracted and 100 ml of toluene was added before re introducing the mixture into a clean decantation funnel. This procedure was repeated several times, until the top organic phase had become transparent to the naked eye. The final washed aqueous particle suspension was then left to settle overnight, and the supernatant was finally removed to minimise the volume of liquid to be removed during subsequent freeze-drying.

The nanoparticle suspension was freeze-dried by plunging the flask containing the suspension into liquid nitrogen, and subliming the water by pumping at a background pressure of 10 mTorr. The resulting dry powder was composed of nanoparticles encapsulated in a matrix of sodium chloride (see FIG. 17-1). This powder could be easily redispersed in water, yielding particles with an average particle size around 200 nm (see FIG. 17-2) and a narrow size distribution (see FIG. 17-3).

Example 16

Synthesis of Cis-Platin Doped Nanoparticle Using Process 4

A cis-platin solution (solution 2) was prepared by dissolving 0.16 g cis-platin (0.53 mmol) in 100 ml of a dilute ammonia solution (10 wt %). Triton X-114 (10.74 g, 20 mmol) and 11.52 ml of solution 2 (32 mmol equivalent of $H_2O$) were added sequentially to 100 ml of toluene, and the resulting micro-emulsion was homogenised by shear-mixing at 8000 rpm for 1 minute. The emulsion was then stirred at 300 rpm and 0.3 ml of TMOS (2 mmol) was added. After stirring for 90 minutes, 50 ml of a 1 M NaCl solution was added to the emulsion and the resulting suspension was transferred to a decantation funnel. The suspension was then washed and freeze-dried according to the procedure described in Example 15.

Example 17

Synthesis of Ultra-Small (i.e. <100 nm) Copper Doped Silica Particles

A copper tetraamine solution (i.e. solution 3) was prepared by dissolving 40 mg of $Cu(NO_3)_2.3H_2O$ (0.17 mmol) in 5 ml of concentrated ammonia (28 wt % $NH_3$). Triton NP-9 (7.77 g, 12.6 mmol) and 0.710 ml of solution 3 (23.5 mmol equivalent of $H_2O$) were added sequentially to 100 ml of cyclohexane, and the resulting micro-emulsion was homogenised by shear-mixing at 8000 rpm for 1 minute. The emulsion was then stirred at 500 rpm and 0.796 ml of TEOS (3.6 mmol) was added. After continuous stirring for 24 hours, 50 ml of demineralised water was added to the emulsion and the resulting suspension was transferred to a decantation funnel. After standing for 12 hours, the emulsion had separated into two phases. The aqueous phase was extracted, mixed with cyclohexane (100 ml) and transferred to a clean decantation funnel. This procedure was repeated several times, until the top organic phase was transparent to the naked eye. A TEM micrograph (FIG. 18-1) of the dried particles indicates that their diameter is ca. 50 nm. Photon correlation spectroscopy of the particle suspension confirmed that the average particle size in solution was 51 nm (FIG. 18-2).

Example 18

Influence of the Surfactant to Alkoxide Molar Ratio (S) on the Average Size of Cu Doped Silica Nanoparticles Nanoparticles were synthesised according to the procedure in examples 15 using the following emulsion compositions:

3 S R Triton X-114 TMOS Solution 1 2 16 18 g (35 mmol) 2.66 g (17 mmol) 10 ml (559 mmol) 10 16 22.49 (44 mmol) 0.665 g (4.3 mmol) 12.6 ml (700 mmol)

Here, S and R refer to the surfactant-to-alkoxide molar ratio and the water-to-surfactant molar ratio, respectively.

The resulting particles were filtered and analysed by SEM (see FIG. 19), which revealed that an increase in S leads to a corresponding decrease in the particle size.

Example 19

Influence of the Water to Alkoxide Molar Ratio on the Average Size of Cu Doped Silica Nanoparticles Nanoparticles were synthesised according to the procedure in examples 15 using the following emulsion compositions:

4 S R Triton X-114 TMOS Solution 1 10 8.8 21.54 g (40 mmol) 0.596 ml (4 mmol) 6.34 ml (352 mmol) 10 1.6 21.54 (40 mmol) 0.596 ml (4 mmol) 1.15 ml (64 mmol)

The corresponding freeze-dried powders were re-suspended in distilled water and characterised by PCS (see FIG. 20). Both particle size distributions exhibited a peak at ca. 150 nm, although the polydispersity increased significantly with decreasing water-to-surfactant mole ratio.

Example 20

Influence of the Concentration of NaCl on the Quantity of Surfactant Retained on the Washed Particles Nanoparticles were synthesised according to the procedure described in Example 15, using 21.44 g of Triton X-114 (40 mmol), 0.596 ml of TMOS (4 mmol) and 11.53 ml of solution 1 (640 mmol equivalent of $H_2O$). After formation of the nanoparticles, the sample was separated into two batches. A 50 ml aliquot of distilled water was added to the first batch, while 50 ml of 0.1M NaCl solution was added to the second. The two suspensions were then washed according to the procedure described in Example 15 and subsequently filtered and dried overnight at 60° C. A sample of each dry powder was then characterised using thermal analysis. The corresponding weight losses associated with desorption/pyrolysis of the surfactant are shown in the following table:

5 Residual Surfactant (wt %) Without NaCl 3.8 With 0.1 M NaCl 2.4

Example 21

Synthesis of Particles by Process 3

A 10 ml sample of TEOS (45 mmol) was dissolved in 40 ml of ethanol and 0.87 ml of an Orange II dye solution at pH=2 (prepared according to the procedure outlined in Example 1) was then added. The resulting solution was stirred for 90 minutes, before adding 0.87 ml of an Orange II dye solution at pH=9.05. The mixture was stirred for an additional 90 minutes, prior to the drop-wise addition of 200 ml of dilute ammonia solution (3 wt %). The resulting suspension was aged quiescently for 12 hours and then centrifuged at 5000 rpm for 15 minutes. The orange solid thus obtained was finally dried at 60° C. for 12 hours. A SEM micrograph of the resulting powder is presented in FIG. 21.

Example 22

Synthesis of Copper Doped Transition Metal Oxide Nanospheres

A copper tetraamine solution (i.e. solution 4) was prepared by dissolving 8.45 g of $Cu(NO_3)_2.3H_2O$ (35 mmol) in 40 ml of concentrated ammonia solution (28 wt % $NH_3$) and diluting the resulting solution to 100 ml with distilled water. Triton NP-9 (19.5 g, 32 mmol) was dissolved in 150 ml of cyclohexane and a microemulsion was subsequently produced by adding 1.125 ml of solution 4 (62 mmol equivalent of $H_2O$) and homogenising the resulting mixture by shear-mixing at 8000 rpm for 1 minute. The microemulsion was then maintained with stirring at 500 rpm.

In a dry nitrogen glove box, 1.83 g (6.4 mmol) of titanium isopropoxide (or 2.78 ml of Zr n-propoxide or 1.639 ml of Al sec-butoxide) was dissolved in 5 ml of cyclohexane. This solution was then added, outside the glove box, to the stirred NP-9/solution 4/cyclohexane emulsion and the resulting mixture was stirred for 2 hours at 500 rpm. A 100 ml aliquot of 1M NaCl was then added to the suspension, and the aqueous layer was washed and freeze-dried according to the procedure outlined in Example 15.

Example 23

Synthesis of $TiO_2/SiO_2$ Mixed Oxide Particles Doped with Orange H by Process 1

Solution 5 was prepared by mixing 0.05 g of Orange II with 20.0 ml of concentrated (70%) nitric acid and diluting with demineralised water to a total volume of 100 ml. The concentrations of $HNO_3$ and Orange II in the final solution were 2.22 M and 0.5 mg/ml, respectively.

A solution containing 1.53 ml of ethanol and 0.47 ml of solution 5 ($EtOH:H_2O:HNO_3$ mole ratio=1:1:0.04) was added dropwise to a mixture of TEOS (5.92 ml, 26.5 mmol) in ethanol (1.53 ml), and the resulting mixture agitated in a Cole Palmer Model 8892 ultrasonic bath for 15 minutes. An aliquot of titanium tetraisopropoxide (1.53 ml, 5.2 mmol) was then added, and the complex alkoxide mixture was sonicated for an additional 15 minutes, and then refluxed for four hours.

A 10 g sample of sorbitan monooleate (23 mmol) was mixed with 100 ml of kerosene in a 250 ml conical flask and stirred for ca. 30 minutes with a magnetic follower, to ensure complete dissolution of the surfactant. A 1.40 ml aliquot of solution 5 was added dropwise to the stirred solution, followed by addition of the complex alkoxide mixture. The resulting sample was stirred for 110 minutes, yielding $SiO_2/TiO_2$ mixed oxide microspheres. The final product was filtered, washed with three 20 ml aliquots of kerosene to remove residual surfactant, dried for 24 hours at ambient temperature and then dried overnight at 60° C. An SEM micrograph of the resulting microspheres is shown in FIG. 22.

It should be appreciated that various other changes and modifications may be made to the embodiment described without department from the spirit and scope of the invention.

What is claimed is:

1. A process of preparing controlled release ceramic particles, comprising:
    (a) providing a reverse micelle solution that is the product of mixing a surfactant with an apolar solvent;
    (b) providing a precursor solution that is the product of combining a gel precursor selected from the group consisting of a silica-based gel precursor, an alumina-based gel precursor, a titanium dioxide-based gel precursor, an iron oxide-based gel precursor, a zirconium dioxide-based gel precursor and a combination thereof, a catalyst, a condensing agent, and a polar solvent, wherein at least one of the reverse micelle and precursor solutions contains an active material that is soluble in the polar solvent; and then (c) combining the reverse micelle solution and the precursor solution to generate droplets of the precursor solution in the reverse micelle solution, such that, within the droplets, ceramic particles form that (i) contain the active material and (ii) are porous to the extent of allowing controlled release of the active material, whereby the active material is substantially homogeneously dispersed within each of the particles and throughout the particles.

2. The process of claim 1, wherein the condensing agent is water.

3. The process of claim 2, wherein the polar solvent is water.

4. The process of claim 1, wherein the gel precursor is selected from the group consisting of a silica precursor, an alumina precursor, a titania precursor, and a combination thereof.

5. The process of claim 4, wherein the gel precursor is a silica precursor.

6. The process of claim 5, wherein said silica precursor is selected from the silicates, the silsequioxanes, poly-silsequioxanes, the silicon alkoxides, functionalized alkoxides, and a combination thereof.

7. The process of claim 5, wherein said silica is biodegradable and biocompatible.

8. The process of claim 1, wherein said surfactant is selected from sorbitan esters, alkylarylpolyether, alcohol ethoxylates, aerosol OT, and sodium bis(2-ehtylhexyl) sulfosuccinate, and a combination thereof.

9. 1626 The process of claim 1, wherein said catalyst is selected from sulfuric acid, phosphoric acid, HCl, HNO$_3$, acetic acid, tartaric acid, succinic acid, salicylic acid, NaOH, KOH, ammonium hydroxide, Ca(OH)$_2$ and a combination thereof.

10. The process of claim 1, wherein said active material is selected from pharmaceuticals for human applications, hormones, proteins, drugs for veterinarian applications, fertilizers, pesticides, herbicides, insecticides, biocides, and perfumes.

11. The process of claim 1, wherein the precursor solution has a pH in the range of 1 to 14.

12. The process of claim 1, comprising bringing the droplets into contact with an aqueous solution of an ionic salt such that the ceramic particles are dispersed into the aqueous solution.

13. The process of claim 12, wherein the suitable ionic salt is selected from NaCl, KI, KBr, NaI, LiCl, LiBr, LiI, CaCl$_2$, MgCl$_2$, NH$_4$NO$_3$, NaNO$_3$, KNO$_3$, LiNO$_3$, and a combination thereof.

14. The process of claim 12, further comprising freeze drying the aqueous solution to form a solid comprised of unaggregated ceramic particles within a matrix of the ionic salt.

15. An assemblage of controlled release ceramic particles that is the product of a process according to claim 1.

16. An assemblage of controlled release ceramic particles that is the product of a process according to claim 2.

17. An assemblage of controlled release ceramic particles that is the product of a process according to claim 3.

18. An assemblage of controlled release ceramic particles that is the product of a process according to claim 4.

19. An assemblage of controlled release ceramic particles that is the product of a process according to claim 13.

20. An assemblage of controlled release ceramic particles that is the product of a process according to claim 14.

* * * * *